(12) United States Patent
Casse et al.

(10) Patent No.: US 11,529,482 B2
(45) Date of Patent: Dec. 20, 2022

(54) METHOD AND APPARATUS FOR CONFIGURING A MEDICAL DEVICE

(71) Applicant: Fisher & Paykel Healthcare Limited, Auckland (NZ)

(72) Inventors: Benjamin Wilson Casse, Auckland (NZ); David Robert Keith Walker, Auckland (NZ); Sheldon Luke Nunes, Auckland (NZ); Christopher Harding Campbell, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 842 days.

(21) Appl. No.: 16/343,350

(22) PCT Filed: Oct. 20, 2017

(86) PCT No.: PCT/IB2017/056521
§ 371 (c)(1),
(2) Date: Apr. 18, 2019

(87) PCT Pub. No.: WO2018/073793
PCT Pub. Date: Apr. 26, 2018

(65) Prior Publication Data
US 2019/0240433 A1 Aug. 8, 2019

Related U.S. Application Data

(60) Provisional application No. 62/411,432, filed on Oct. 21, 2016.

(51) Int. Cl.
*A61M 16/00* (2006.01)
*G16H 40/63* (2018.01)
(Continued)

(52) U.S. Cl.
CPC ...... *A61M 16/024* (2017.08); *A61M 16/0051* (2013.01); *G16H 40/40* (2018.01);
(Continued)

(58) Field of Classification Search
CPC ............ A61M 16/024; A61M 16/0051; A61M 2205/3553; A61M 2205/3584;
(Continued)

(56) References Cited

U.S. PATENT DOCUMENTS 10,576,223 B2 * 3/2020 D'Angelo ......... A61M 16/0051
2003/0236450 A1 12/2003 Kocinski
(Continued)

FOREIGN PATENT DOCUMENTS

WO   WO 01/32069 A2    5/2001
WO   WO 2013/187776 A1   12/2013
WO   WO 2015/179915 A1   12/2015

OTHER PUBLICATIONS

International Search Report; International Application No. PCT/IB2017/056521, filed on Oct. 20, 2017; ISR mailing date: Jan. 29, 2018; 5 pages.
(Continued)

*Primary Examiner* — Steven O Douglas
(74) *Attorney, Agent, or Firm* — Knobbe Martens Olson and Bear, LLP

(57) ABSTRACT

A method of configuring a medical device for a patient comprising: receiving information relating to a patient, the patient requiring a medical device, determining and/or receiving a medical device configuration for the medical device, the medical device configuration being suitable for the patient, uploading the medical device configuration to a server, wherein, the medical device configuration on the
(Continued)

server is for later download by the device when the patient has received their medical device and activated the medical device.

27 Claims, 19 Drawing Sheets

(51) Int. Cl.
  *G16H 40/40* (2018.01)
  *G16H 20/40* (2018.01)
(52) U.S. Cl.
  CPC ..... *G16H 40/63* (2018.01); *A61M 2205/3553* (2013.01); *A61M 2205/3584* (2013.01); *A61M 2205/3592* (2013.01); *A61M 2205/505* (2013.01); *G16H 20/40* (2018.01)
(58) Field of Classification Search
  CPC .... A61M 2205/3592; A61M 2205/505; G16H 40/40; G16H 40/63; G16H 20/40
  See application file for complete search history.

(56) References Cited

U.S. PATENT DOCUMENTS

| 2008/0114689 | A1 | 5/2008 | Psynik et al. |
| 2009/0107498 | A1 | 4/2009 | Plattner et al. |
| 2011/0073107 | A1* | 3/2011 | Rodman ................ G16H 40/63 141/2 |
| 2015/0199479 | A1* | 7/2015 | Semen ................... G06F 21/44 705/3 |
| 2015/0302159 | A1* | 10/2015 | Casse ................. G06F 16/9554 705/2 |
| 2018/0369522 | A1 | 12/2018 | Bassin et al. |

OTHER PUBLICATIONS

Extended European Search Report; Application No. 17861926.8; dated May 8, 2020; 11 pages.

* cited by examiner

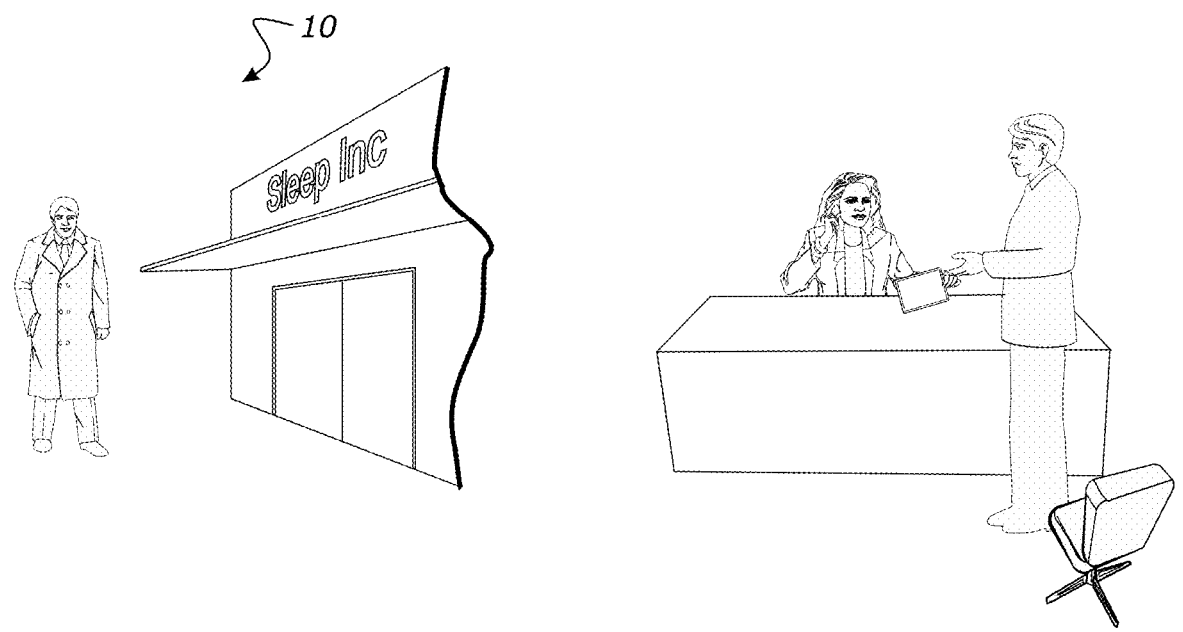
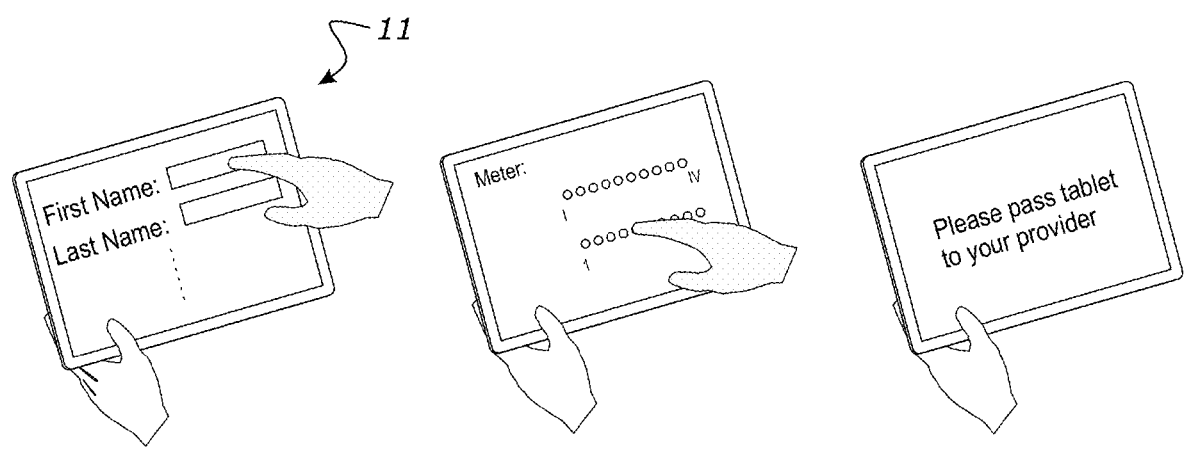
Patient set up in InfoSmart
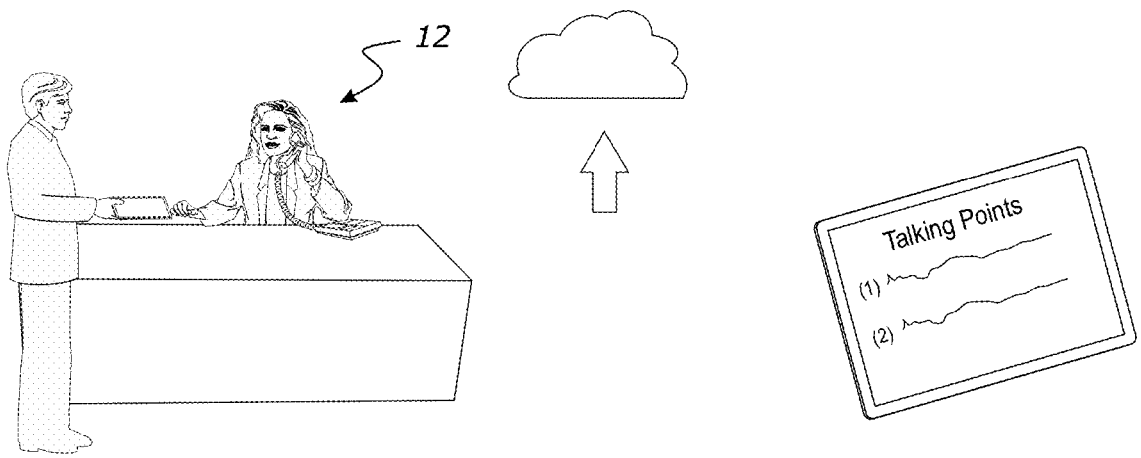
FIGURE 3A

*FIGURE 6B*

METHOD AND APPARATUS FOR CONFIGURING A MEDICAL DEVICE

FIELD OF THE INVENTION

The present invention relates to a method and apparatus for determining and/or configuring the function of a medical apparatus, and in particular although not limited a breathing assistance apparatus, such as a CPAP apparatus or high flow therapy apparatus.

BACKGROUND

When a patient (user) requires a CPAP apparatus to assist with their obstructive sleep apnoea, they visit a dealer who provides a consultation, who then selects a device with a suitable function and prescription to treat the patient's breathing disorder.

SUMMARY OF INVENTION

It is an object of the present invention to provide a method, system and/or apparatus to allow for configuration of a CPAP apparatus or other breathing apparatus (or more generally "medical device")

In one aspect the present invention comprises a method of configuring a medical device for a patient comprising: receiving information relating to a patient, the patient requiring a medical device, determining and/or receiving a medical device configuration for the medical device, the medical device configuration being suitable for the patient, uploading the medical device configuration to a server, wherein, the medical device configuration on the server is for later download by the device when the patient has received their medical device and activated the medical device.

In one embodiment the medical device configuration is associated on the server with at least some of the information relating to the patient.

In one embodiment the medical device configuration is associated on the server with the medical device.

In one embodiment the medical device configuration is associated with the medical device by a medical device identifier.

In one embodiment the medical device is associated on the server with at least some of the information relating to the patient.

In one embodiment the method further comprising providing the medical device to the patient in an unconfigured or default state.

In one embodiment the method further comprising the medical device downloading the device configuration from the server on activation of the medical device.

In one embodiment the method further comprises downloading the configuration to the medical device.

In one embodiment the method further comprises providing a user entry device to the patient from which to receive the patient input.

In one embodiment the user entry device provides questions pertaining to the likelihood of the user to use the medical device according to a prescription In one embodiment the medical device is a breathing assistance apparatus.

In one embodiment the medical device is one of: CPAP apparatus, Bilevel apparatus, High Flow Therapy apparatus, or other breathing assistance apparatus.

In another aspect the present invention comprises a medical device adapted to receive a configuration comprising: a communications interface to communicate with a server and receive a configuration from the server, a processor to receive the configuration and configure the medical device.

In one embodiment the configuration is created as in any one of the method paragraphs above.

In one embodiment the medical device is one of: CPAP apparatus, Bilevel apparatus, High Flow Therapy apparatus, or other breathing assistance apparatus.

In another aspect the present invention comprises a system for configuring a medical device comprising: a server with a communications interface to receive a configuration for a medical device and provide that configuration to a medical device.

In one embodiment the configuration is created as in any one of the method paragraphs above.

In one embodiment the medical device is one of: CPAP apparatus, Bilevel apparatus, High Flow Therapy apparatus, or other breathing assistance apparatus.

In another aspect the present invention comprises a method of providing and/or configuring a medical device comprising: receiving information relating to a patient, the patient requiring a medical device, determining and/or receiving a medical device configuration for the medical device the medical device configuration being suitable for the patient, uploading the medical device configuration to a server, wherein the medical device configuration on the server is for transfer to the medical device, and providing the medical device to the patient.

In one embodiment the method further comprises the step of configuring the medical device by downloading the medical device configuration from the server onto the medical device.

In one embodiment the method further comprises step of configuring the medical device by transferring the medical device configuration from the server onto the medical device using a wireless data transfer technology such as NFC or RFID tags.

In one embodiment the medical device downloads the medical device configuration from the server onto the medical device after patient has received their medical device and activated the medical device.

In one embodiment a medical device provider configures the medical device by downloading the medical device configuration from the server onto the medical device prior to providing the medical device to the patient.

In one embodiment a medical device provider configures the medical device by transferring the medical device configuration from the server onto the medical device using wireless data transfer technology prior to providing the medical device to the patient when the device is off.

In one embodiment the provider provides the medical device to the patient by shipping the medical device to the patient, in a configured or unconfigured state.

In one embodiment the medical device implements a default configuration, such as Auto CPAP, prior to being configured via download or transfer, or if the configuration process fails.

In one embodiment the medical device is a breathing assistance apparatus.

In one embodiment the medical device is one of: CPAP apparatus, Bilevel apparatus, High Flow Therapy apparatus, or other breathing assistance apparatus.

In one embodiment the medical device is unable to provide therapy until configuration of the medical device has been determined to be complete.

In one embodiment a message is sent to a medical device provider if the download has not been confirmed within a predetermined amount of time.

At least some embodiments described remove at least part of the manual entry required to set a patient up for follow up and monitoring, and allow a patient to be provided a device, without any configuration needing to be performed on that device prior to the patient receiving it. This will enable a healthcare provider to give a patient a device in an unopened box, without the time cost of having to unbox, power up, configure and re-box the device. It also enables new distribution models where devices can be shipped directly to patients from a remote, third party, or manufacturers warehouse, without a healthcare provider needing to touch the product prior to delivery.

At least some embodiment described provide a network enabled pressure support device which is configured to communicate with a remote server. The remote server being configured to communicate with a database containing a record for each device that has been provided to a patient. Each device record may contain a related device configuration profile which contains one or more of the following pieces of information:

- Device configuration settings (for example pressure set points, operating modes i.e., AUTO or CPAP, humidity set points).
- Activation commands for therapeutic features (for example a code to enable a feature that is already present on a device but not active, such as Sensawake™, humidity, or expiratory relief)
- Software modules for therapeutic features (for example an application to provide a feature that is not present on a device (such as Sensawake™ (pressure reduction on detection of wakefulness) or humidity).
- Full or partial device firmware (for example a new firmware version or alternate firmware version containing a different pressure delivery mode)

When a device is powered up, if it has not previously received a configuration profile, it attempts to communicate with the remote server, providing its serial number and model. On receiving a connection from a device the server attempts to retrieve the configuration profile for the device, indexed by the devices serial number, from the database. On receiving a configuration profile the device will apply the provided settings, and or download and install the referenced software modules or firmware updates. The device will then reconnect to the server to confirm the provided settings and updates have been applied.

In at least some embodiments, a device is prevented from being used therapeutically without the patient's prescription having been applied.

BRIEF DESCRIPTION OF DRAWINGS

Embodiments will be described with reference to the drawings, of which:

FIGS. 3A to 3C show a work flow of a patient, provider, medical device and cloud based environment to enable configuration of the medical device.

Figures 5E, 5F:
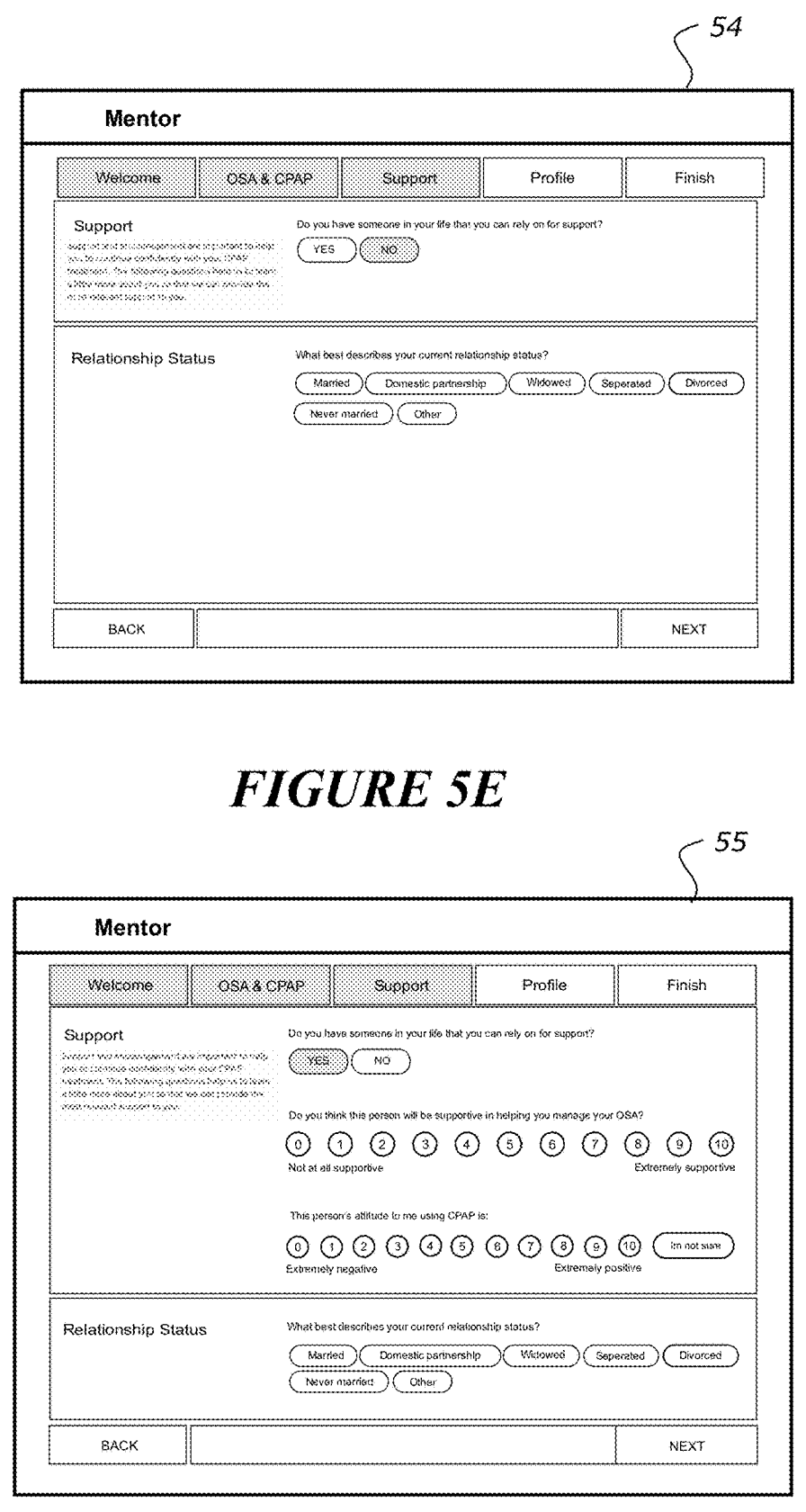

FIGS. 5A to 5I show user entry device screens for obtaining patient responses to build a patient profile.

FIGS. 6A, 6B show a provider screen for assisting consultation with a patient.

DETAILED DESCRIPTION OF EMBODIMENTS

Overview

Figure 1A:
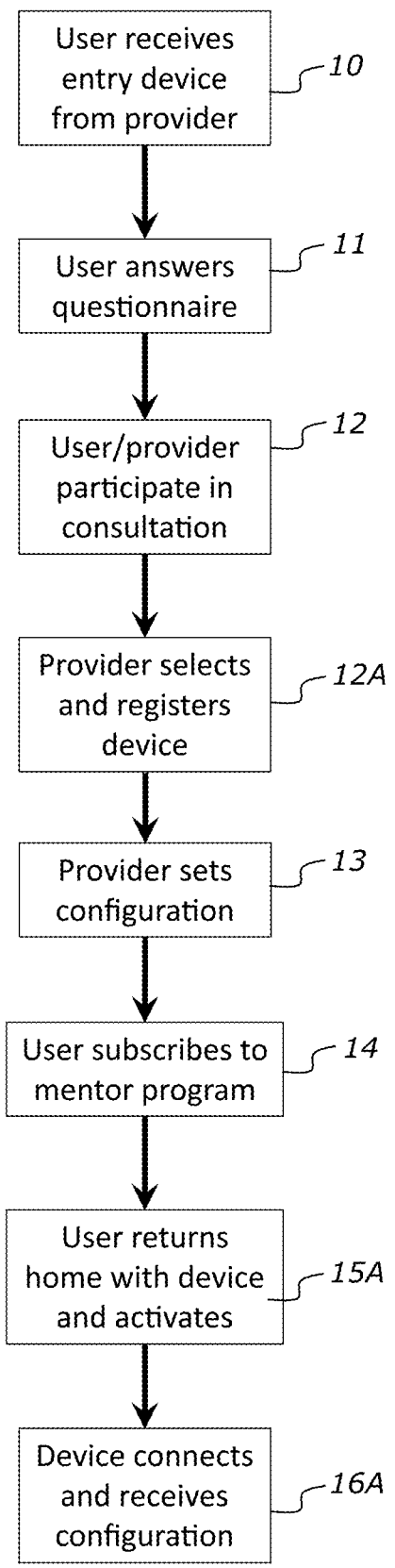
FIG. 1A is a flow diagram of showing the actions of a patient, provider, medical device and cloud based environment to enable configuration of the medical device according to a first exemplary embodiment.
Figure 2A:
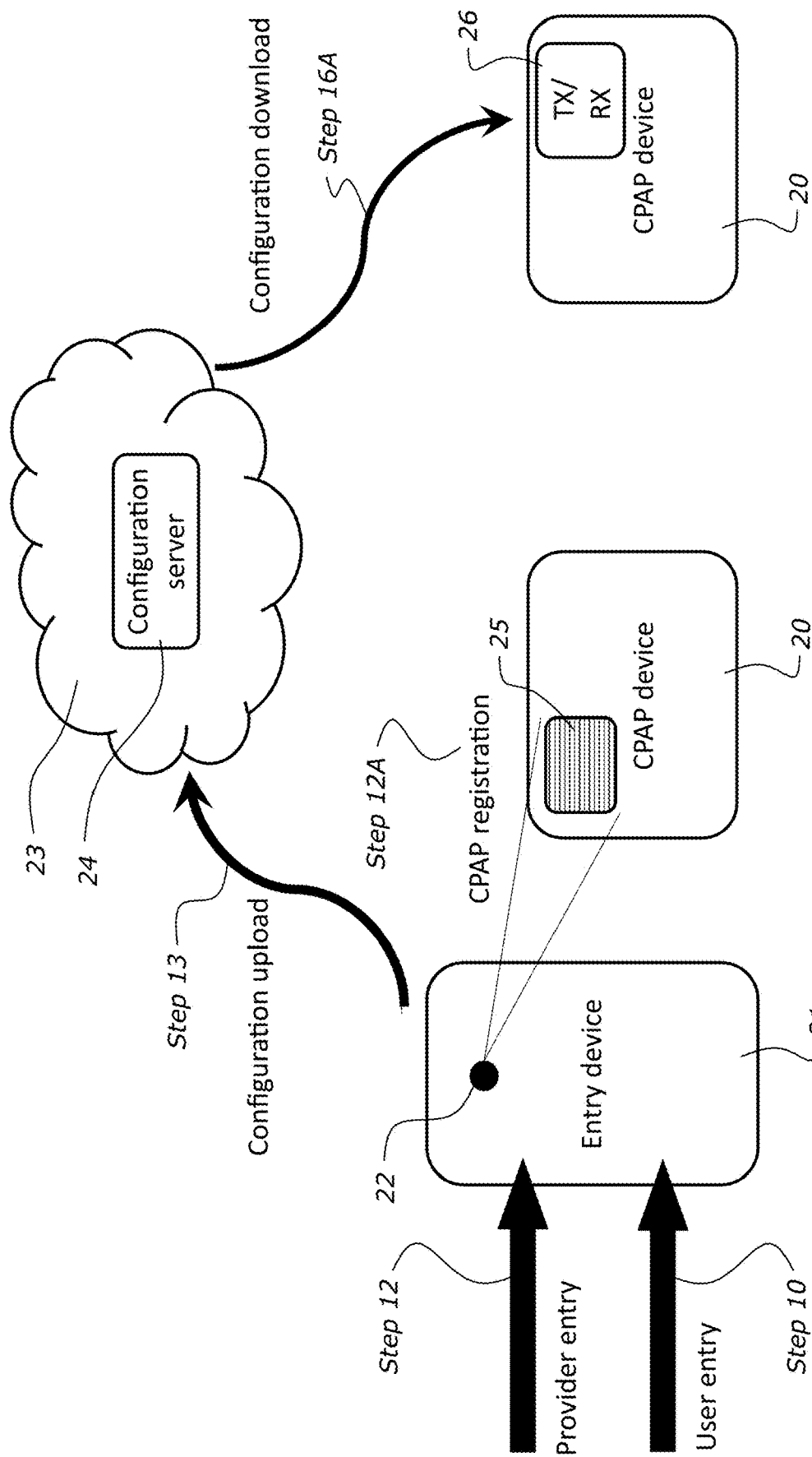
FIG. 2A shows a diagram of a system for configuring a medical device according to a first exemplary embodiment.

FIG. 1A shows a flow diagram of a method of configuring a medical device, and FIG. 2A shows an associated system for configuring a medical device. The medical device 20 could be for example a breathing assistance apparatus such as a CPAP, Bilevel, high flow therapy or other similar breathing assistance apparatus. The method and apparatus described could also relate to other types a breathing assistance apparatus, or more generally other types of medical device. The remaining description will describe embodiments in relation to a CPAP breathing assistance apparatus 20, but this is by way of example only, and should not be considered limiting. The method described comprises actions from a patient, CPAP apparatus provider, computer system/cloud environment and CPAP apparatus. This is provided for context and it will be appreciated that it is not essential for the invention to encompass all the actions and parties/hardware that implement those actions. The invention is defined by way of the claims.

A patient (user) who requires a CPAP breathing assistance apparatus 20 (hereinafter: CPAP apparatus or CPAP device) to treat a breathing disorder visits a provider of such a CPAP apparatus, such as a dealer (DME). The patient receives a user entry device 21 from the provider, step 10, for use in entering information that helps build a profile of the patient (patient profile) and helps assist the CPAP apparatus provider to determine which type of CPAP apparatus is required, and what its configuration should be, to treat the patient. It also provides information to the dealer to help them advise the patient on the CPAP apparatus use and provide support. The user entry device 21 could be any suitable device, such as a computer, a tablet, such as an iPad or similar, a mobile telephone or other mobile device. Optionally, the user entry device could be a manual form of capturing profile information, such as a paper questionnaire, which is filled in by hand or similar. The user entry device provides a questionnaire to the patient, the response to which assist with building the patient profile.

The patient answers the questionnaire, step 11, by entering responses on the user entry device 21, which elicits information from the user to help build the patient profile to aid the provider in determining a suitable CPAP apparatus 20 and its required configuration for the patient. A trained expert at the provider then receives this information and participates in a consultation, step 12, with the patient to assess their treatment requirements. The trained expert selects a suitable CPAP apparatus and also determines the required configuration, which can include its functionality, setup parameters, the prescription it provides (in the case of a CPAP apparatus, the pressure prescription) and the like. The CPAP configuration, or portions of it, could also or alternatively be determined by a computer program and/or a physician. The trained expert then registers the selected CPAP apparatus and associates it with the patient (for example, by information related to the patient—that is, patient profile), preferably in a cloud computing environment 23 (server), step 12A. Among other things, this can comprise a configuration server 24. They also set the configuration of the CPAP apparatus, which is stored in the cloud computing environment 23 as a CPAP configuration profile on the server 24 (for example in the form of a record, in a database of such records for many CPAP apparatus), step 13. Alternatively or additionally, the CPAP apparatus can also be associated with the medical device configuration in the cloud computing environment (server), for example by way of a medical device identifier. The medical device configuration can alternatively or additionally also be associated with the patient (for example, by information relating to the patient—that is, patient profile)

Optionally, the trained expert may assist the patient to subscribe to a mentor programme, step 14, which might be an app based programme to assist the patient in the use of the CPAP apparatus. The provider then gives the selected CPAP apparatus to the patient to take home for use, step 15A. At that stage, the CPAP apparatus does not have a configuration, or has a default configuration. Once home, the user activates the CPAP apparatus, step 15A. The CPAP apparatus connects itself to the cloud computing environment, and downloads the configuration, step 16A, which it uses to configure itself to provide the functionality, setup configurations and prescription as decided by the provider. The patient can then use the CPAP apparatus for treatment in the usual way.

Figure 1B:
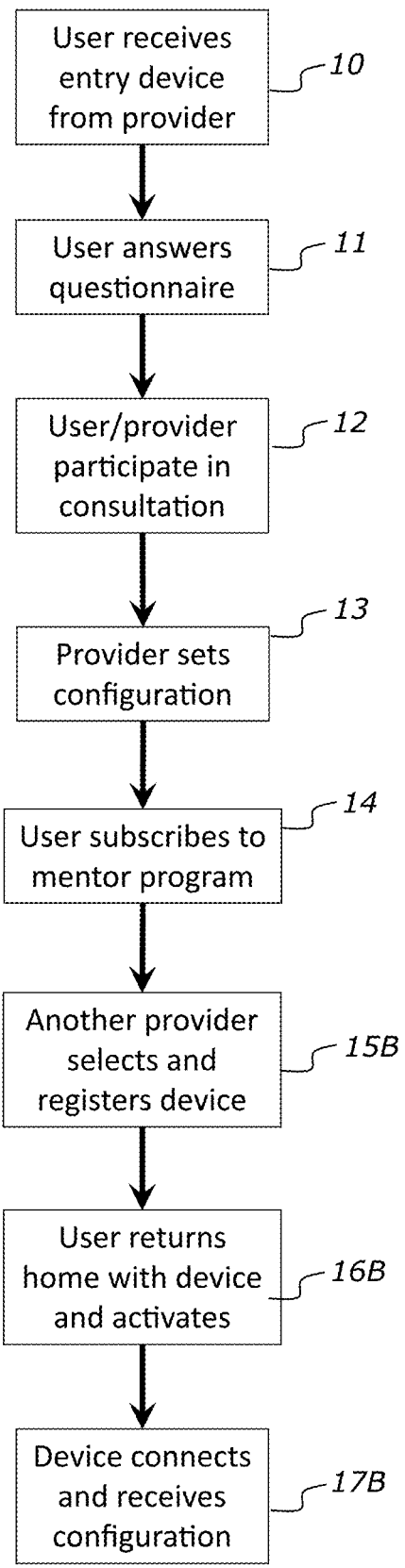
FIG. 1B is a flow diagram of showing the actions of a patient, provider, medical device and cloud based environment to enable configuration of the medical device according to another exemplary embodiment.
Figure 1C:
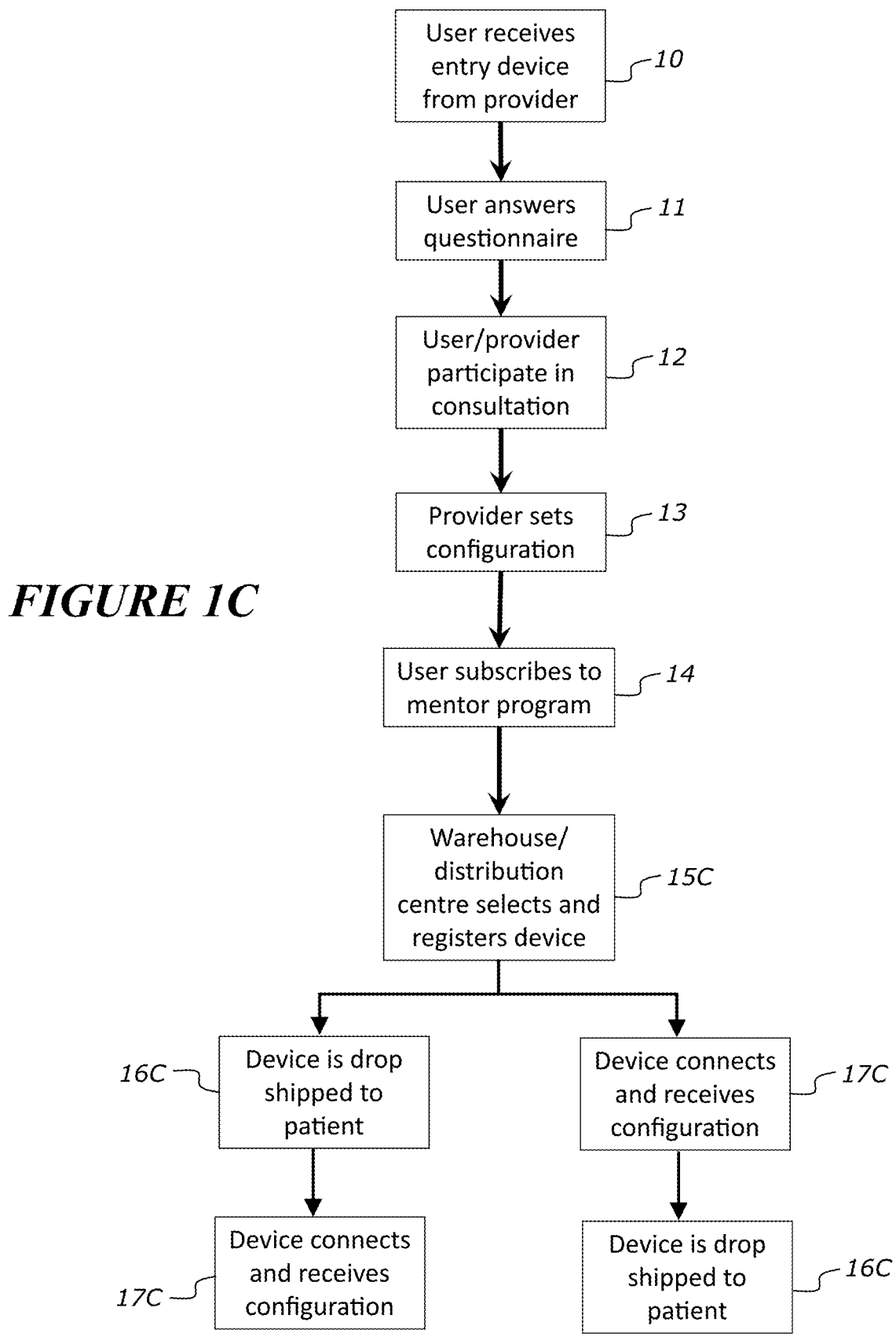
FIG. 1C is a flow diagram of showing the actions of a patient, provider, medical device and cloud based environment to enable configuration of the medical device according to another exemplary embodiment.

FIGS. 1B and 1C show flow diagrams of alternative methods of configuring a medical device, and FIGS. 2B to 2E show an associated system for configuring a medical device.

Figure 2B:
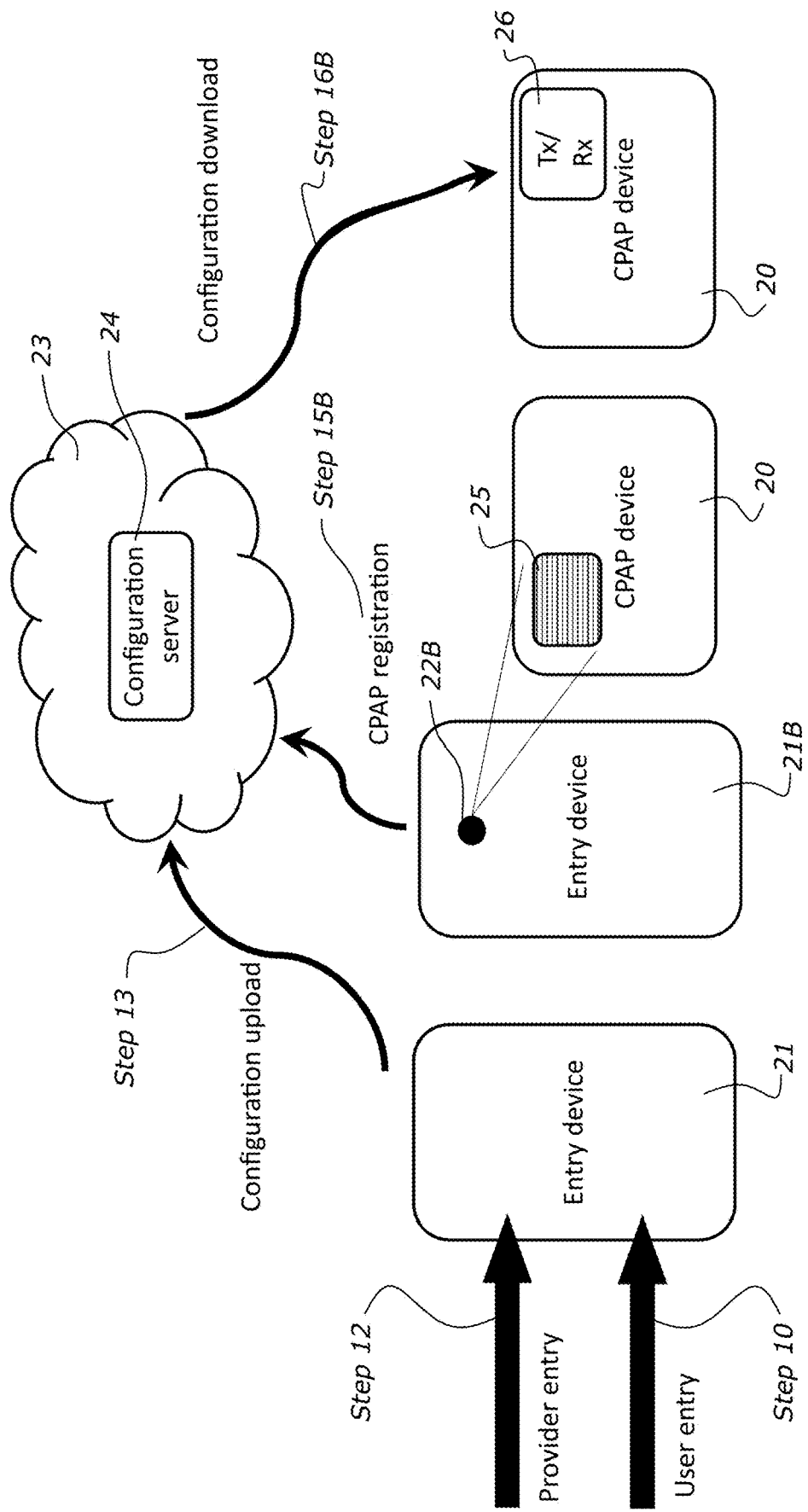
FIG. 2B shows a diagram of a system for configuring a medical device according to another exemplary embodiment.

As one alternative depicted in FIGS. 1B and 2B, the trained expert of the provider does not supply a CPAP apparatus, but rather that CPAP apparatus is provided and registered by a third party provider.

Figure 2C:
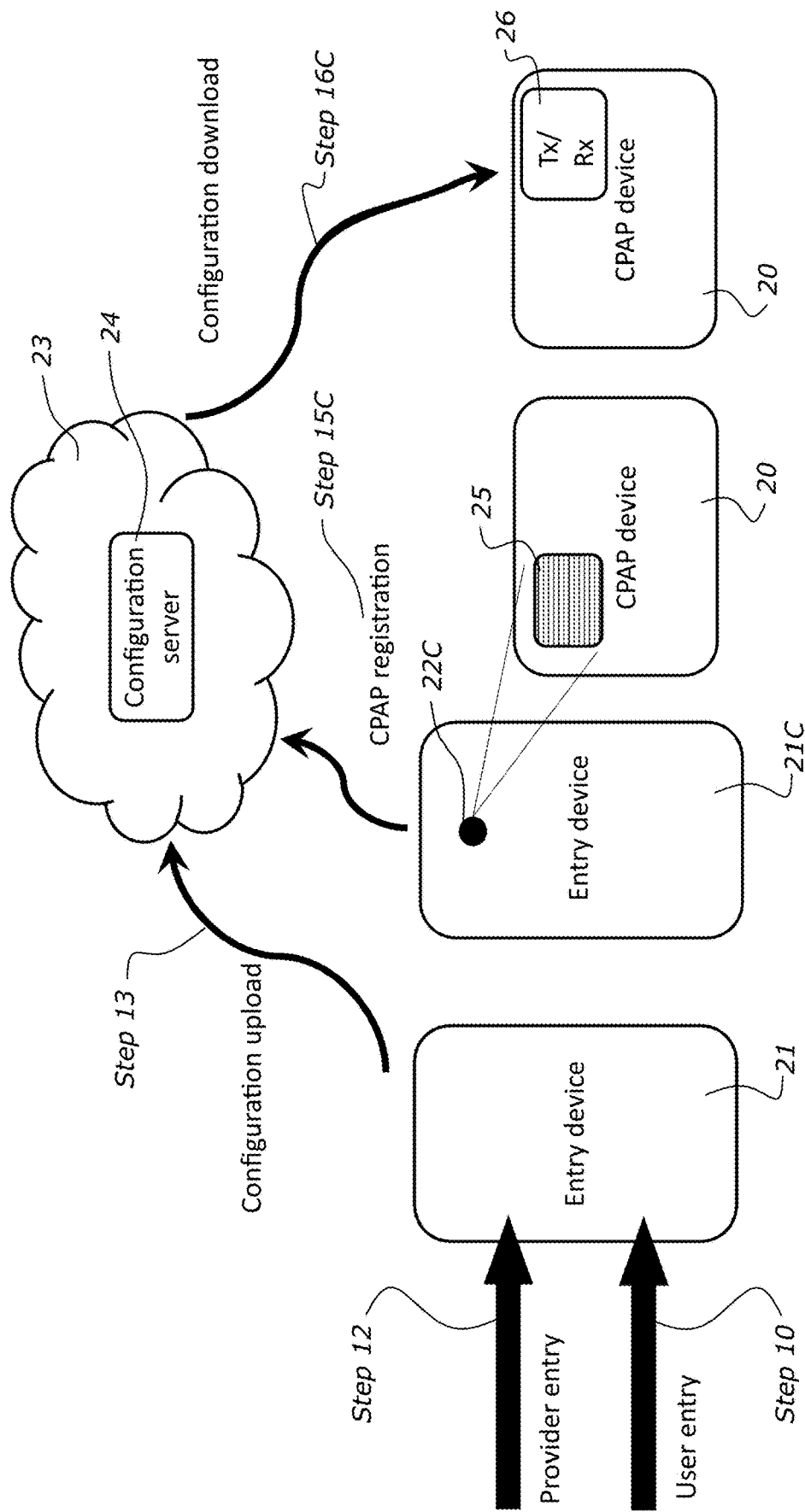
FIG. 2C shows a diagram of a system for configuring a medical device according to another exemplary embodiment.
Figure 2D:
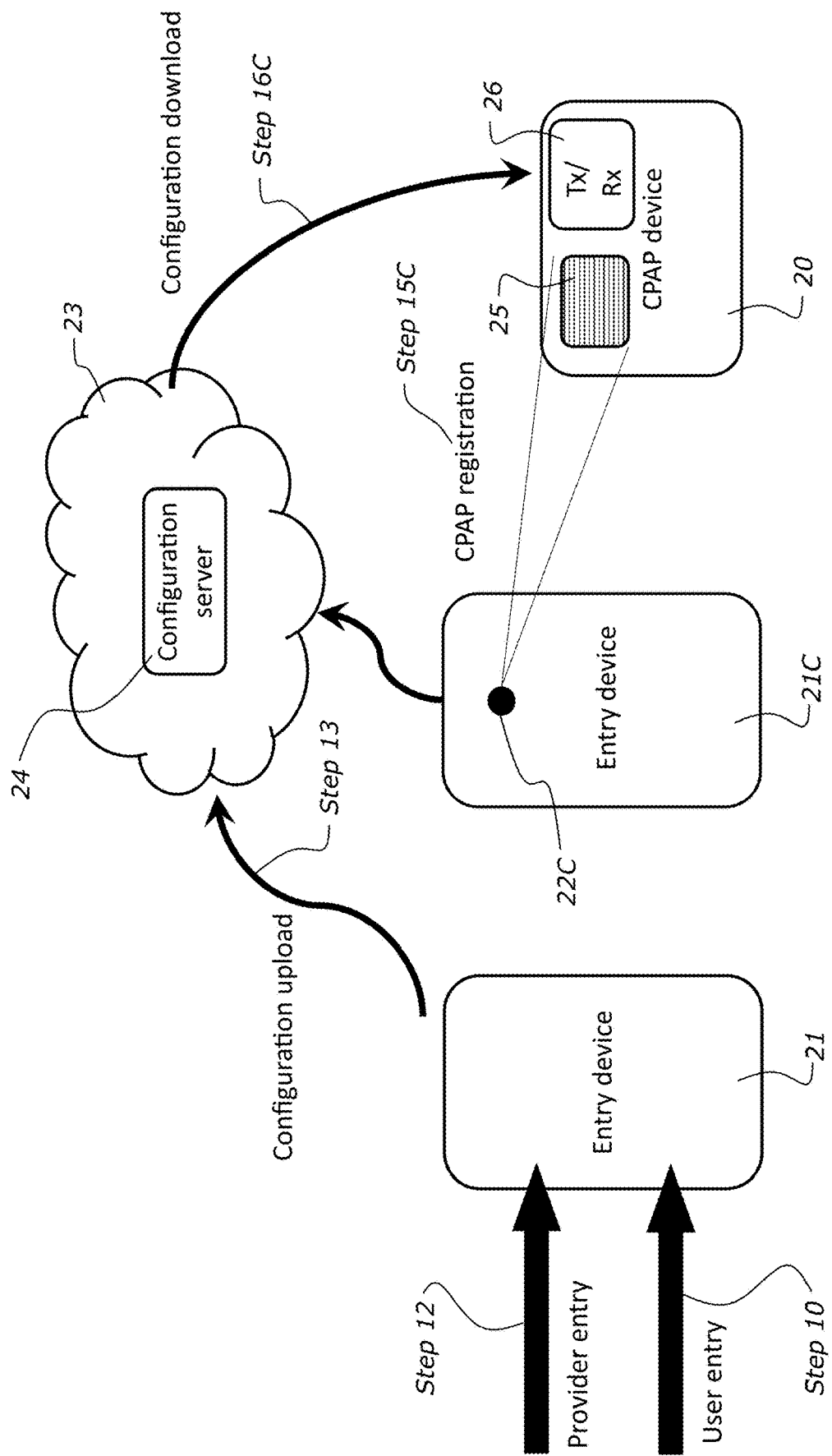
FIG. 2D-2E show a diagram of a system for configuring a medical device according to other exemplary embodiments.

As another alternative depicted in FIGS. 1C, 2C and 2D, the CPAP apparatus can be registered and configured in a warehouse or other distribution centre using cloud download or NFC, and drop-shipped with its configuration to the user's place of use. Alternatively, the CPAP apparatus can be drop shipped unconfigured, for later configuration by the user.

Exemplary embodiments will now be described.

First Exemplary Embodiment

An exemplary embodiment will now be described in detail with reference to FIGS. 1A, 2A, and 3A to 6B.

Figure 3B:
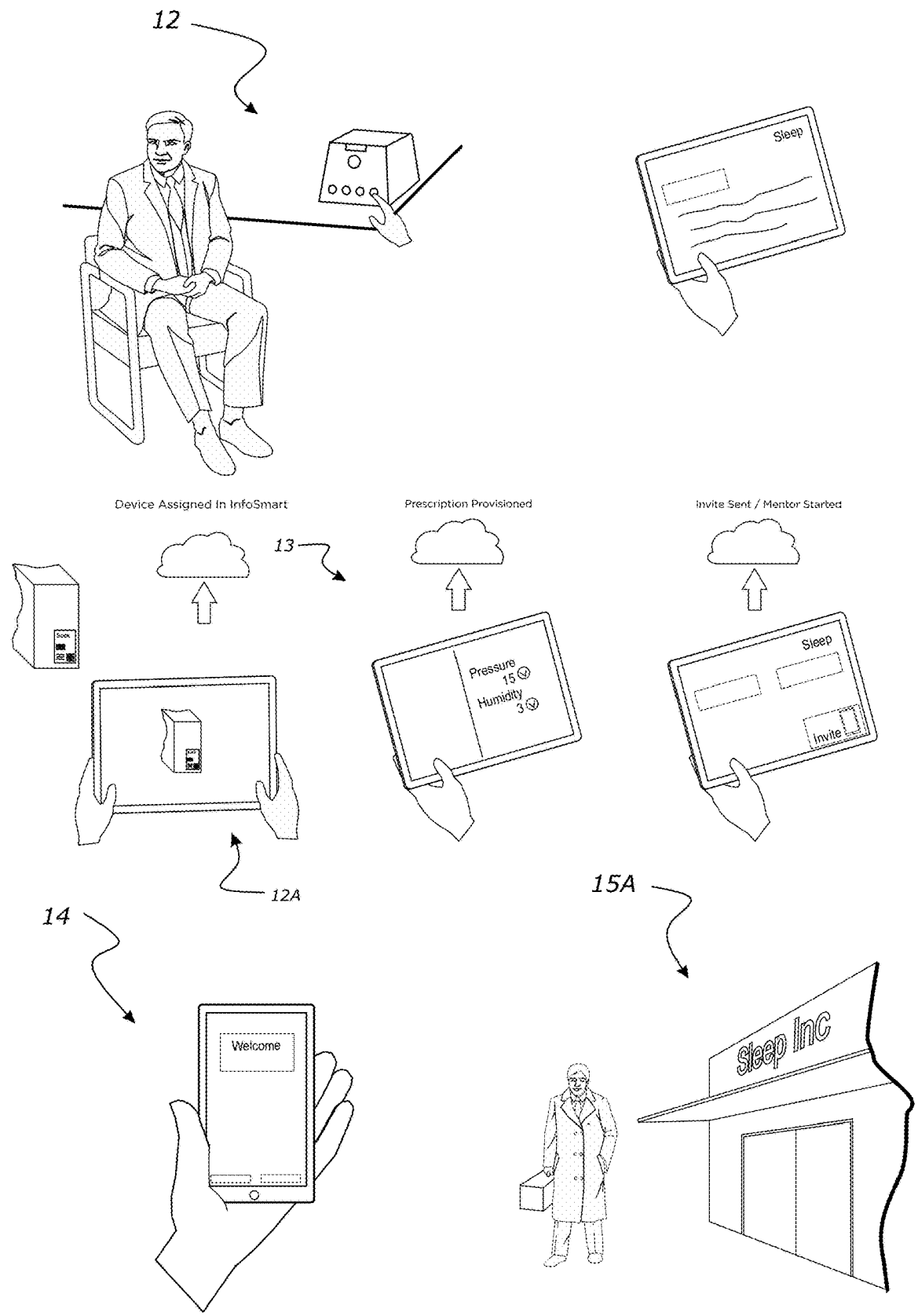
Figure 3C:
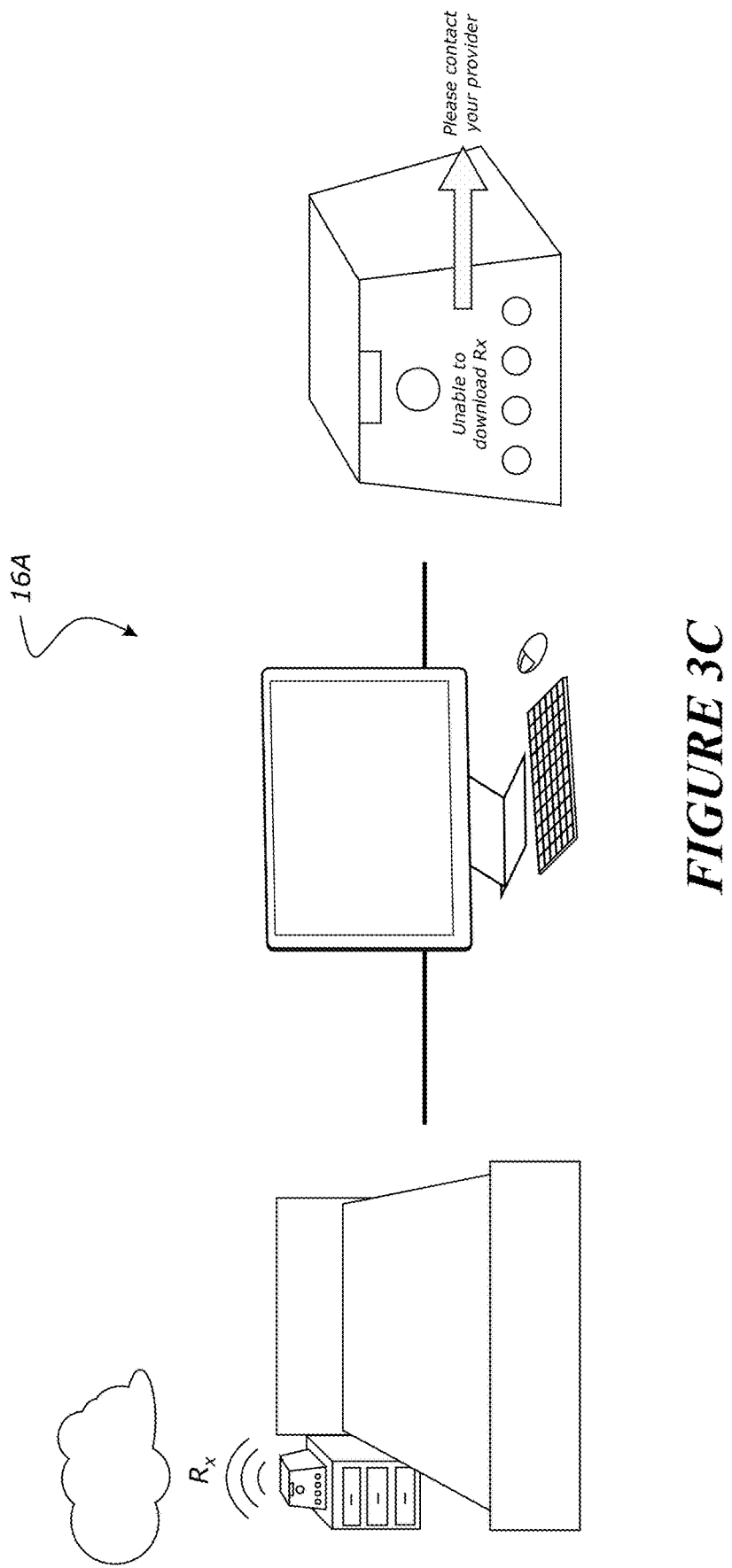
Figure 4:
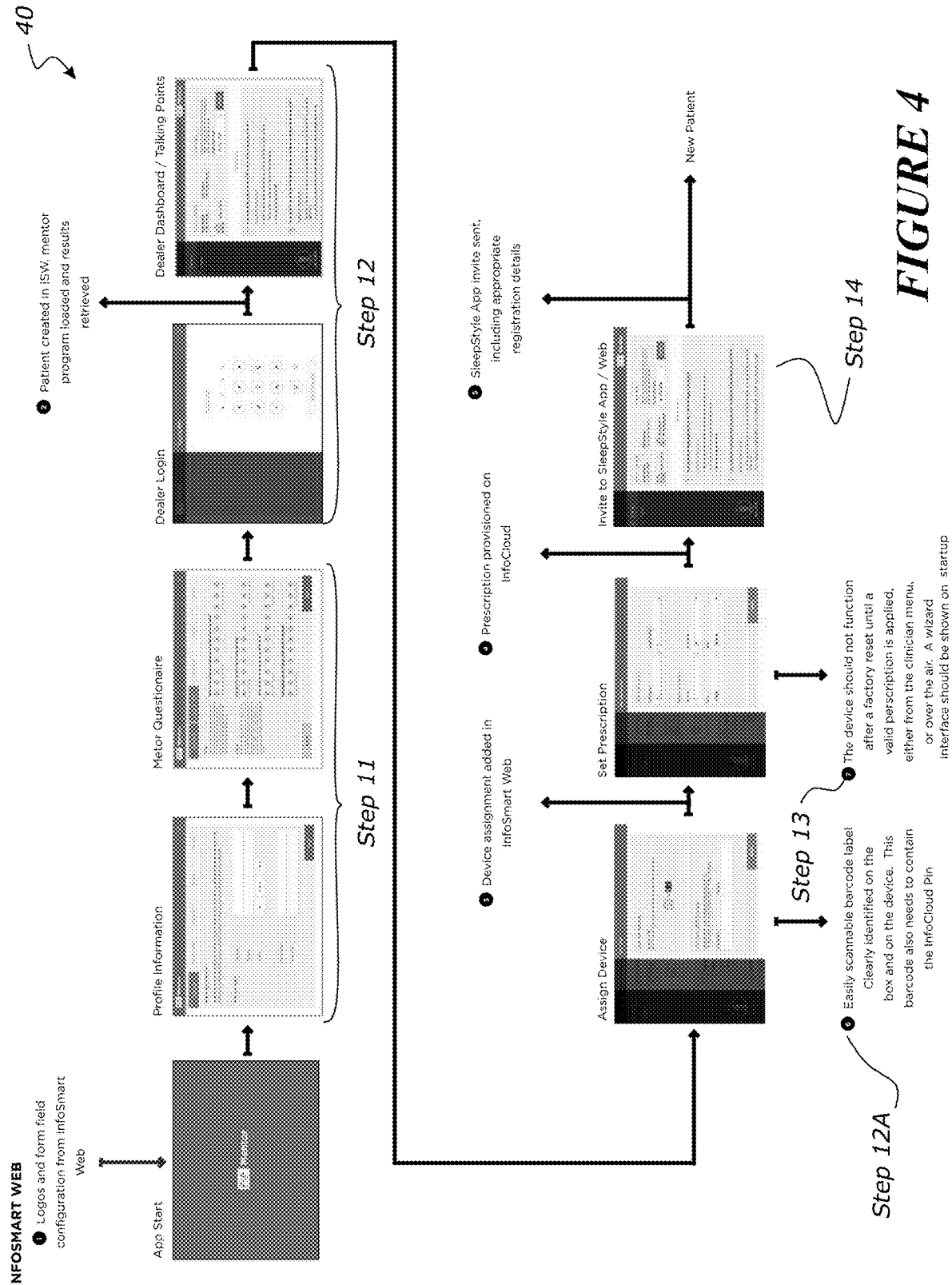
FIG. 4 shows screenshots of a user entry device showing the high-level work flow for obtaining information for the purposes of configuring a medical device.

FIGS. 3A-3C show a storyboard walk-through of the method, FIG. 4 shows workflow for eliciting patient profile information and providing a configuration profile, and FIGS. 5a to 6B show various screenshots of the user device and the provider device for eliciting patient profile information and CPAP apparatus configuration information.

Referring to FIGS. 1A, 2A and 3, the patient goes to a provider, step 10, and at reception is given a user entry device, such as a tablet 21. The user entry device has an app with a user interface providing screens with a questionnaire that captures the patient information from the patient to build the patient profile (See FIGS. 5A to 5I), step 11. The captured information comprises personal details, and also responses to the questions in the questionnaire that determine the needs and nature of the patient. The information can be entered into the user entry device 21 before the consultation with the trained expert, such as in the reception waiting area.

Referring to FIG. 4 and FIGS. 5A to 5I, the workflow 40 of the entry of the user information using the app will be explained. The app starts, and then a screen/tab is provided that requests user login details, such as a username, password and/or PIN creation (see screens 50 and 51 on FIGS. 5A and 5B). Then a screen 52 is provided (see FIG. 5C) that requests user personal details, such as name, gender, date of birth, contact details and the like.

The app then provides screens (see FIGS. 5D to 5I) presenting a questionnaire to the patient and the patient is then prompted to complete the questionnaire. As an example, the patient is presented with a questionnaire page asking questions that elicit information about their perceptions, nature and other psychological attributes. The questionnaire for example comprises 14 questions, the responses to which create a model identifying the key psychological drivers of a patient in relation to their use or non-use (adherence/non-adherence, or compliance/non-compliance) of the CPAP apparatus 20. The responses also build a personalised support program for a patient, to be delivered via text message or other communication means as will be described later, to support the patient as they embark on the treatment. The questionnaire could comprise questions such as those described in PCT application published as WO2013/187776 which is incorporated herein by reference in its entirety. The user can provide responses by entering information and/or touching buttons on a touchscreen, such as shown on screen 58 on FIG. 5I.

Figures 5A, 5B:
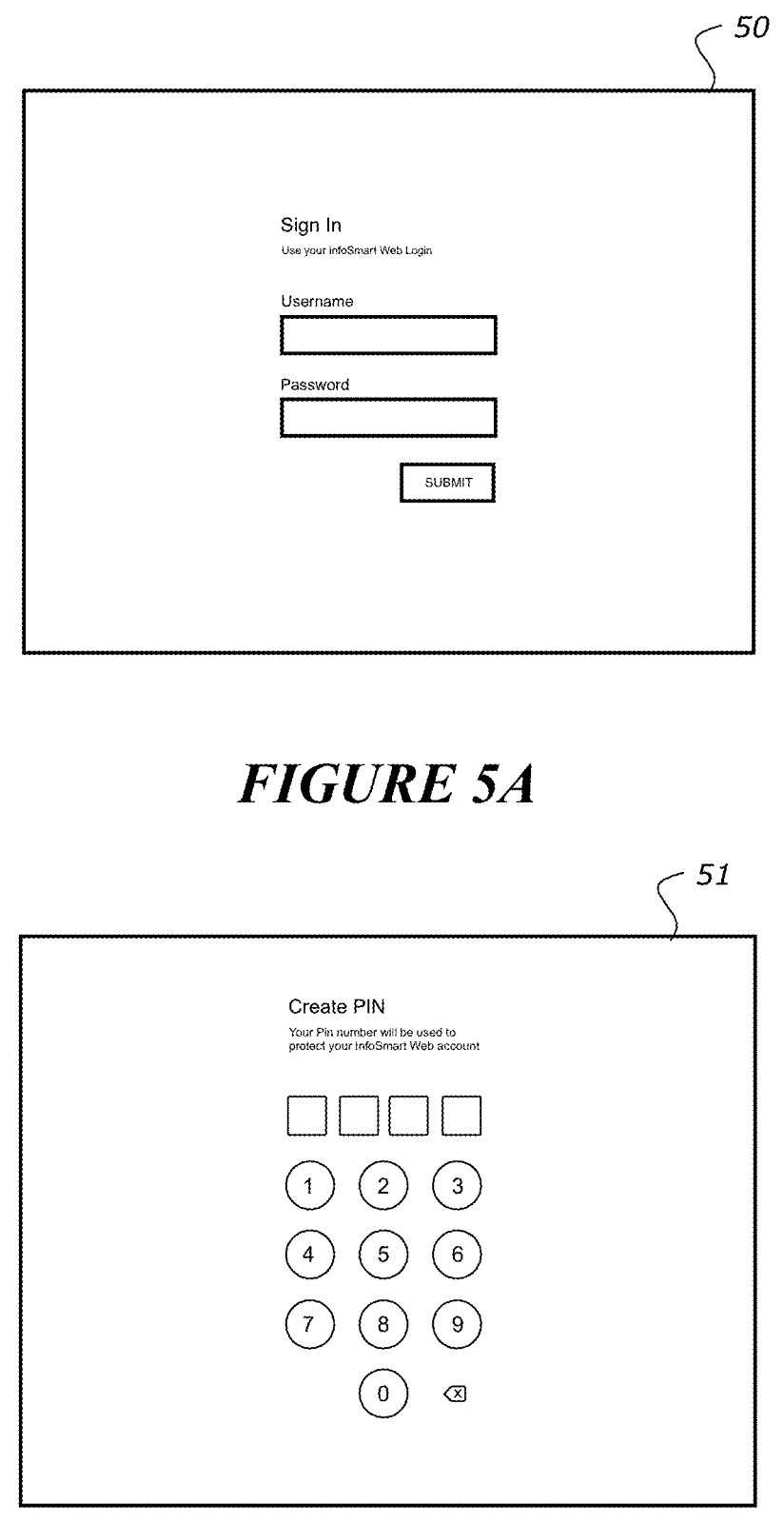
Figures 5C, 5D:
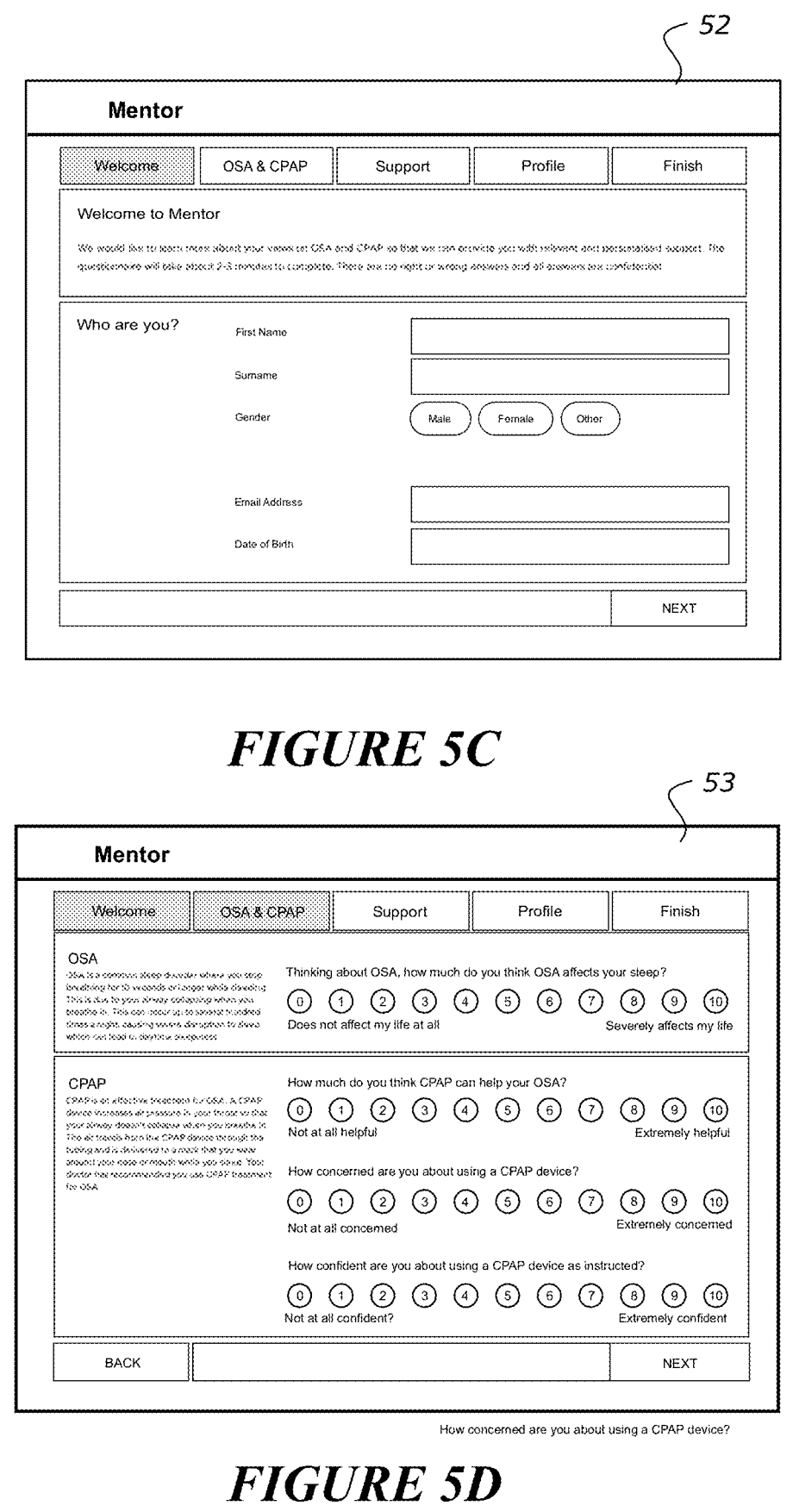

As an example, as shown in FIG. 5D, on a first screen/tab 53, the following questions/statements are asked/posed, and the patient responds.

"Thinking about OSA, how much do you think OSA affects your sleep?"—response on scale of 0-10 from "it does not affect my life at all" to "severely affects my life"

"How much do you think CPAP can help your OSA?"—response on scale of 0-10 from "not at all helpful" to "extremely helpful"

"How concerned are you about using a CPAP device?"—response on scale of 0-10 from "not at all concerned" to "extremely concerned"

"How confident are you in using a CPAP device as instructed?"—response on scale of 0-10 from "not at all confident" to "extremely confident"

The patient is prompted to answer/respond in a suitable manner, for example in this embodiment by indicating a number that indicates how much they agree with the question/statement. This can be done by pressing buttons on the touch screen of the user entry device, such as shown on screen 58 on FIG. 5I. On entering the information, this is stored for later retrieval within the user entry device 21.

The patient can then be presented with further pages/screens/tabs, such as shown in FIGS. 5E to 5H to ask further questions that elicit responses to psychological and other characteristics of the patient. The user can move forward and backwards through the pages to enter and revise answers/responses as required.

Other questions presented, which can be answered or responded to in a similar manner, include:

FIG. 5E, screen 54
"Do you have someone in your life that you can rely on for support?"—Yes/No
"Which best describes your current relationship status?"—Married, domestic partnership, widowed, separated, divorced, never married, other.

FIG. 5F, screen 55
"Do you have someone in your life that you can rely on for support?"—Yes/no
"Do you think this person will be supportive in helping you manage your OSA?" response on scale of 0-10 from "not at all supportive" to "extremely supportive"
"This person's attitude to me using CPAP is?"—response on scale of 0-10 from "extremely negative" to "extremely positive"

Figures 5G, 5H:

FIG. 5G, screen 56
"Which racial or ethnic group do you most identify with?"—American Indian or Alaska native, Asian, Black or African-American, native Hawaiian or other Pacific Islander, white or American European, Hispanic/T no, other.
"What is your highest qualification?"—I did not complete high school, high school graduate/GED, associate's degree/specialised program, bachelors degree or higher
"what is your occupation?"—Self-employed, homemaker, student, unable to work, employed for wages, retired, other
"what is your household income?"—0-$29, 999; $30,000-$59,999; $100,000 or more; prefer not to answer FIG. 5H, screen 57
"how do you feel about your sleep testing experience?"—response on scale of 0-10 from "extremely negative" to "extremely positive"

Examples of how a user might answer these questions by pressing touch screen answers is shown on screen 58 in FIG. 5I.

Figures 6A, 6B:
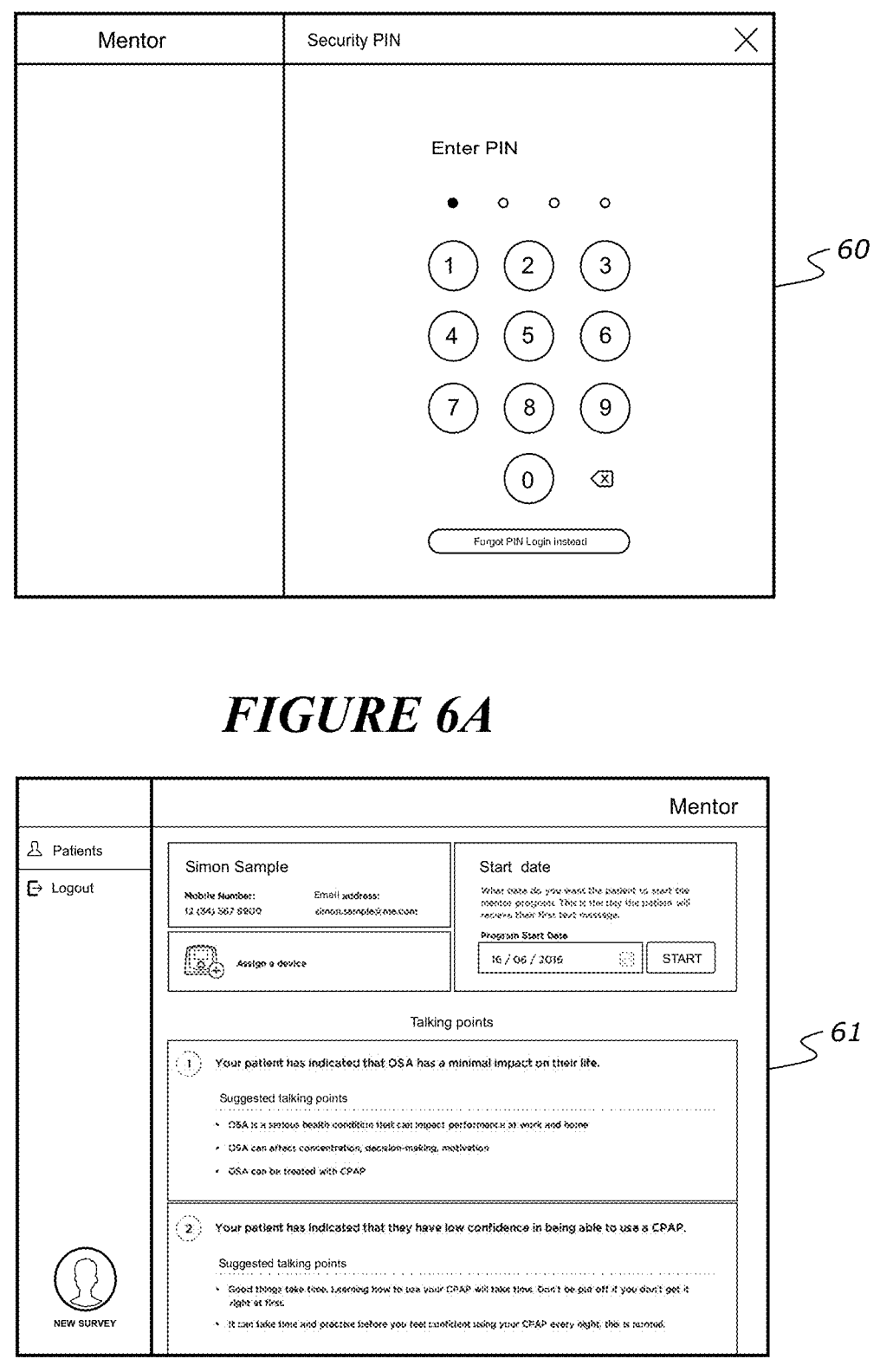

Once all the questions are responded to, the user is ready for the consultation, step 12. They take their tablet or other user entry device 21 with them to the trained expert when they have the consultation. In the consultation, the patient hands over the user entry device to the trained expert, who is able to enter a PIN or other authentication—see FIG. 6A, screen 60—to access patient dashboard—see FIG. 6B, screen 61, that provides patient profile information based on the questionnaire answers and also the answers themselves. The app presents the trained expert with talking points, which have been identified, selected or otherwise determined based on the questionnaire responses. The talking points provide meaningful areas of discussion, allowing the expert to focus the conversation on areas of greatest benefit to the patient leading to time saved in trying to find out this information through conversation. An example of such talking points is shown in FIG. 6B For example, referring to FIG. 6B for a user that has indicated that OSA has minimal impact on their life, the expert may be prompted to talk about the following points OSA is a serious health condition that can impact performance at work and home. OSA can affect concentration, decision-making, motivation OSA can be treated with CPAP Likewise, for a patient who has indicated that they have low confidence in being able to use CPAP, the expert might be prompted to talk about the following.

Good things take time. Learning how to use CPAP will take time. Don't be put off if you don't get it right at first It can take time and practice before you feel confident using your CPAP every night, this is normal.

Next, the expert can choose a suitable configuration for the CPAP apparatus (being a suitable configuration for the patient) and train the patient on the use of the CPAP apparatus, for example using a demo unit they have on their desk. The configuration can be selected/define by the expert, by a physician and/or by a computer program. They do not need to open a box of a new unit for the patient. Once the expert has finished training, they can provide a boxed up CPAP apparatus 20 to the patient. This will have a default configuration, or no configuration.

Figure 7:
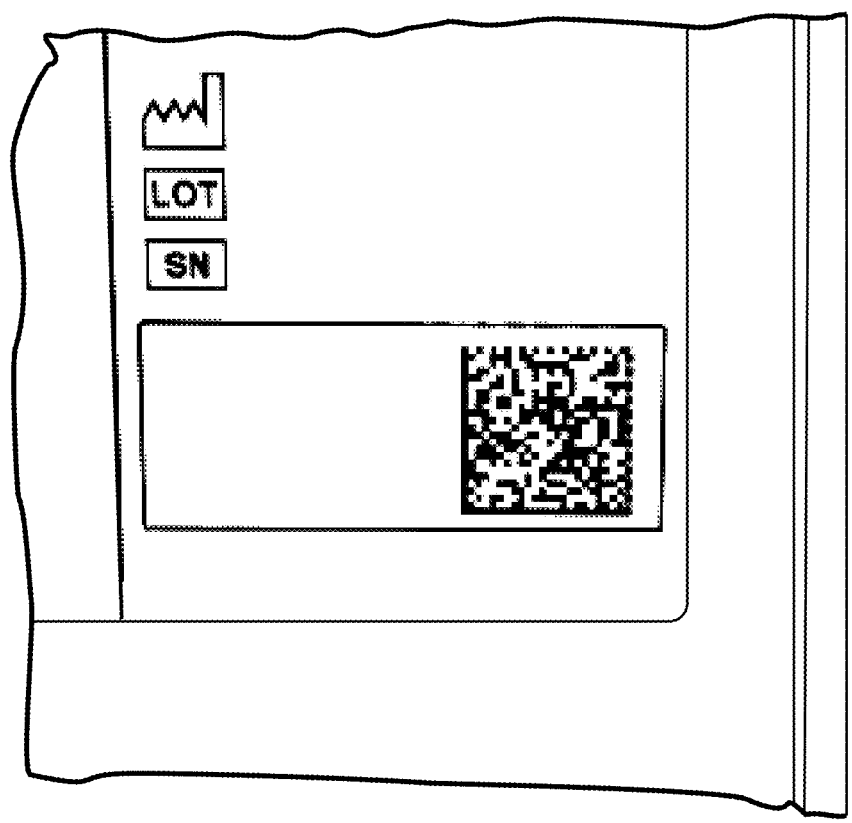
FIG. 7 shows identifying mark on a box for a medical device used in configuration of the device.

Prior to the box being taken away, the expert will register the CPAP apparatus, step 12A. This could be by way of a "assign device" button on the app of the user entry device such as shown in FIG. 6B. Upon pressing the assign device button, a camera 22 of the user entry device is turned on. The expert can point the camera at a label 25, such as QR code barcode, serial number or other identifying mark, on the box of the CPAP apparatus (or the device itself) that the expert will give to the patient (see FIG. 2 and FIG. 7). The app scans the identifying mark, and assigns the patient to the CPAP apparatus in a cloud based database. The identifying mark can be entered manually also. The identifying mark on the CPAP apparatus box preferably contains a serial number of the device, and an identifying number on the device for storage in the database. The identifying mark should be unique in its format from other barcodes and identifying marks on the label so that other such identifying marks are not accidentally scanned as the camera is pointed at the box. Preferably, if there are multiple identifying marks e.g. barcodes, present on the box, the identifying mark for assigning the device and registering it should be clearly identified as that identifying mark that should be scanned or otherwise entered. This could involve bounding and labelling it or wrapping the identifying mark around the edge of the box. The identifying mark also needs to be a format and size that is quickly and accurately able to be scanned by mobile devices et cetera from for example a distance of sent 20 cm at an angle that is comfortable for someone holding a user entry device if the box is on the table top.

The app then communicates with the cloud based server to set up a record for the patient which indicates the patient, their device and then the configuration.

At that point the expert can provide the configuration, step 13.

The configuration profile is then uploaded and stored on the cloud server for later download by the CPAP apparatus so it can self-configure.

As an option, the trained expert then can invite the patient to an app and associated support programme for the patient to assist with the treatment, step 14. If the expert chooses to invite the patient, the patient will receive an email instruction to their own computer or user or mobile device telling them how to download the app on that device and begin monitoring their own therapy progress.

If the provider chooses to start the support programme, the patient gets a welcome text, email, message or other communication asking if they want to join the program. If they do, they begin to receive feedback and encouragement messages.

The patient is then provided with the CPAP apparatus in the box and they return home.

A further set up may be required by the provider to establish monitoring for the patient. They do not need to access the cloud based server to complete set up.

When the patient returns home, they can unbox the CPAP apparatus and turn it on, step 15A. The CPAP apparatus comprises a communications interface 26, such as an internal modem, external modem or the like that connects it to the cloud based server. It downloads configuration profile for the patient from the cloud-based server.

The CPAP apparatus then self-configures itself as per the configuration profile, step 16A.

As an example, a network enabled pressure support device is provided which is configured to communicate with a remote server. The remote server being configured to communicate with a database containing a record for each device that has been provided to a patient. Each device record may contain a related device configuration profile which contains one or more of the following pieces of information:
- Device configuration settings (for example pressure set points, operating modes i.e., AUTO or CPAP, humidity set points).
- Activation commands for therapeutic features (for example a code to enable a feature that is already present on a device but not active, such as Sensawake™, humidity)
- Software modules for therapeutic features (for example an application to provide a feature that is not present on a device (such as Sensawake™ or humidity).
- Full or partial device firmware (for example a new firmware version or alternate firmware version containing a different pressure delivery mode)

When a device is powered up, if it has not previously received a configuration profile, it attempts to communicate with the remote server, providing its serial number and model, step 16A. On receiving a connection from a device the server attempts to retrieve the configuration profile for the device, indexed by the devices serial number, from the database. On receiving a configuration profile the device will apply the provided settings, and or download and install the referenced software modules or firmware updates, step 16A. The device will then reconnect to the server to confirm the provided settings and updates have been applied.

If the user does not activate the device, then the configuration will not be downloaded. Alternatively, if the user does activate the CPAP apparatus but it does not connect properly to the cloud based server, it will not download the configuration. This could provide difficulties, and that no therapy might be provided or a sub-optimal therapy might be provided. In this case, if the configuration has not been downloaded for a certain period, e.g. 2 days, they are provided an alert so they can contact the patient and resolve the matter. As well or alternatively the CPAP apparatus may have a default configuration that will provide at least some therapy and will not be detrimental. The default could be autotitration CPAP, which automatically titrates the pressure provided to the patient based on feedback. However, such a default configuration might not provide optimal therapy, and that could be detrimental to the patient. To stop the default or other incorrect configurations being used long term, the CPAP apparatus could lock out after a certain period of time, such as 2 days, of having no personalised configuration setup. The medical device is unable to provide therapy until configuration of the medical device has been determined to be complete. A message could be provided telling the patient to contact the provider, for example if the download has not been confirmed within a predetermined amount of time.

Further Exemplary Embodiment

Another exemplary embodiment will now be described with reference to FIGS. 1B and 2B. Description provided herein is intended to highlight the differences between this exemplary embodiment and the other exemplary embodiments.

This embodiment is applicable where the dealer does not supply a particular CPAP apparatus 20 that is being recommended, but rather that CPAP apparatus 20 is provided by a competitor. The process (steps 10, 11, 12, 13 and 14) proceeds as normal, except that the patient is not provided with a CPAP apparatus 20 from the provider—they will receive that from another provider. However, the configuration will still have been uploaded to the cloud based server 23, 24 by the trained expert, even though the actual CPAP apparatus 20 is being provided by another provider. Likewise, registration of the CPAP apparatus 20 is done by the other provider—although the registration process is similar to the registration process described in the first exemplary embodiment.

The registration process will now be described in more detail. The trained expert uploads an order number linked to the patient's configuration profile. This makes it possible for other provider to register the CPAP device 20 with the patient. When the patient visits the other provider, the other provider is able to register the CPAP apparatus 20, by linking the serial number of the CPAP apparatus 20 to the correct configuration profile, step 15B. The other provider uses their entry device 21B to either capture the label 25 on the CPAP apparatus 20, using a camera 22B, or manually enters the serial number of the CPAP apparatus 20 into entry device 21B.

When the patient receives the CPAP apparatus 20 from the other provider and takes it home, they can turn on in the usual way, step 16B and get the configuration downloaded and the apparatus configured in the usual way, step 17B.

This is so the provider provides a consultation, and then selects a device with a suitable function and prescription to treat the patient's breathing disorder.

Further Exemplary Embodiment

Another exemplary embodiment will now be described with reference to FIGS. 1C, 2C, 2D and 2E. Description provided herein is intended to highlight the differences between this exemplary embodiment and the other exemplary embodiments.

This embodiment is applicable when an order for a CPAP apparatus 20 is placed and the CPAP apparatus 20 is drop shipped to the patient's home. The process (steps 10, 11, 12, 13 and 14) proceeds as normal, except that the patient is not provided with a CPAP apparatus from the provider—instead the CPAP apparatus 20 is shipped from a warehouse, distribution centre, or some other off-site location. In this case, the warehouse is responsible for registering and configuring the CPAP apparatus 20, although the registration process is similar to the registration process described in the earlier described exemplary embodiments.

The registration process will now be described in more detail. The trained expert uploads an order number that is linked to the patient's configuration profile. This makes it possible to complete the CPAP apparatus registration in a warehouse. When the warehouse receives the order number, CPAP apparatus serial number can be correctly matched to the configuration profile, step 15C. The warehouse personnel uses an entry device 21C to either capture the label 25 on the CPAP apparatus 20, using a camera 22C, or manually enters the serial number of the CPAP apparatus 20 into entry device 21C. Once the registration process is complete, the CPAP apparatus 20 can be drop shipped to the patient ready for use, step 16C. The patient then powers on the CPAP apparatus 20 as per normal for configuration, step 17C.

Alternatively, the CPAP apparatus can be unboxed and turned on, and then configured before being drop shipped to the patient, as shown in FIG. 2D As previously described, the CPAP apparatus 20 comprises a communications interface 26, such as an internal modem, external modem or the like that connects it to the cloud based server 23, 24. It downloads configuration profile for the patient from the cloud-based server 23, 24. The CPAP apparatus 20 is then configured in the usual way, step 16C and can be drop shipped to the patient ready for use, step 17C

Figure 2E:
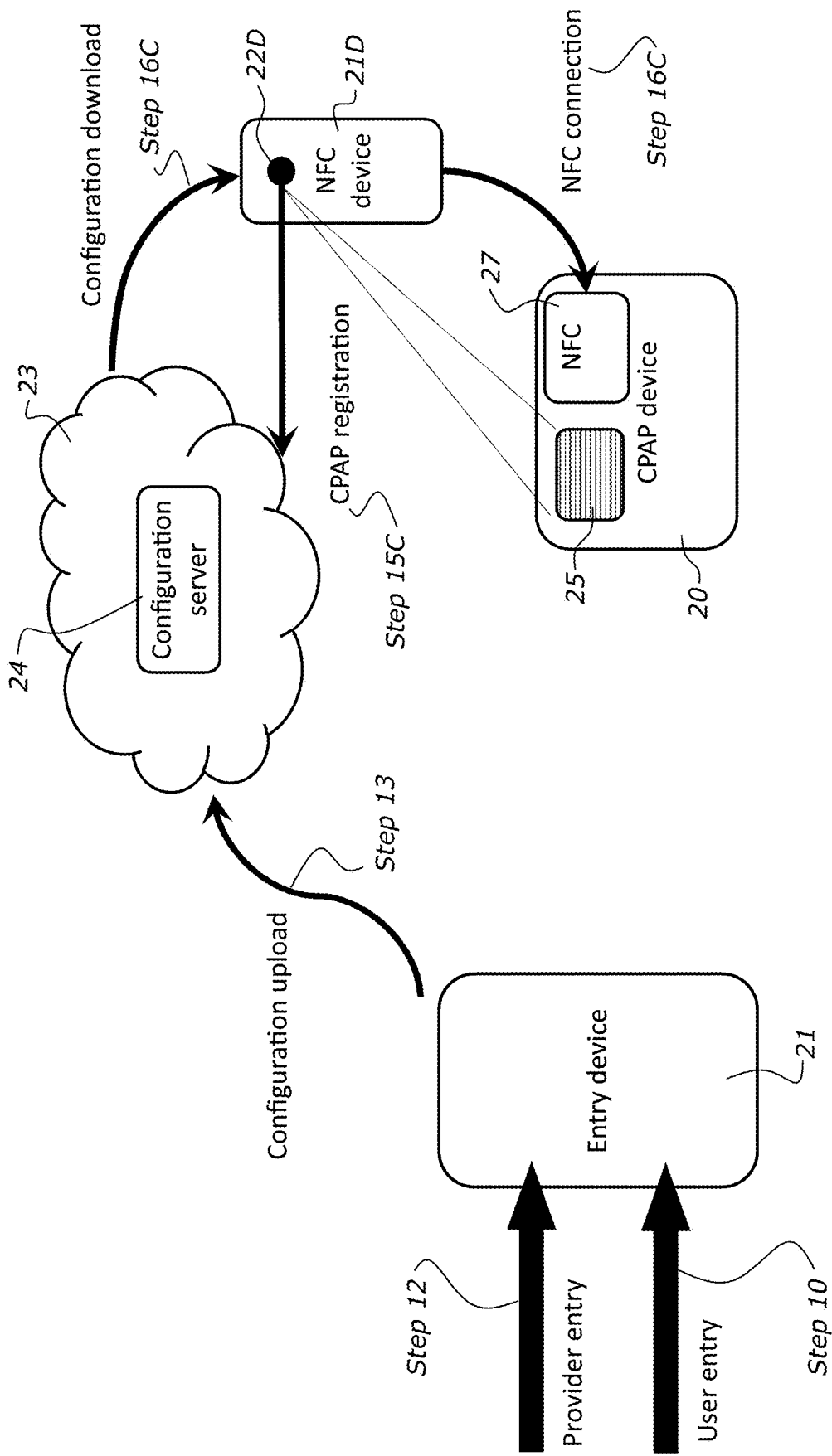

Alternatively, the CPAP apparatus 20 can be registered, step 15C and configured, step 16C in a warehouse or distribution centre while the CPAP apparatus 20 is powered off, and/or still in package using a wireless data transfer technology, as will be explained with reference to FIG. 2E.

Configuration (step 16C) of the CPAP apparatus 20 can be achieved if the CPAP apparatus 20 comprises an embedded smart near-field-communication (NFC) chip 27 (or 'tag') having local memory that can be configured by an NFC-enabled computing device 21D, such as a smartphone, tablet, or the like. To initiate the CPAP configuration process, the NFC-enabled computing device 21D is held close to the NFC tag 27 to create an NFC connection. This allows the NFC-computing device 21D to retrieve information from the CPAP 20 that is relevant for identification, such as serial number and the model for example. The NFC-computing device 21D connects to the remote cloud based server 23, 24. On receiving a connection from the NFC-computing device 21D, the server 24 attempts to retrieve the configuration profile for the CPAP device 20, indexed by the CPAP device's serial number, from the database. Once the correct configuration profile is retrieved, the provided settings and/or referenced software modules and/or firmware updates are downloaded from the cloud based server 23, 24 to the NFC-computing device 21D, step 16C. When an NFC connection is made between the NFC-computing device 21D and the NFC tag 27, the CPAP apparatus 20 is able to apply the provided settings, and/or download and install the referenced software modules or firmware updates. The CPAP device 20 will then reconnect to the NFC-computing device 21D to confirm the provided settings and updates have been applied.

Confirmation that provided settings and updates have been applied can also be relayed from the NFC-computing device 21D to the remote cloud based server 23, 24. At this point, the CPAP apparatus 20 is properly configured, and can be drop shipped to the patient ready for use, step 17C.

The NFC-computing device 21D may also be used for completing CPAP registration instead of the entry device 21C, step 15C, by using a camera 22D to capture the label 25 on the CPAP apparatus 20, or by manually entering the serial number of the CPAP apparatus 20 into the NFC-computing device 21D.

It is possible that other wireless data transfer standards and/or technologies may be used in place of NFC, such as RFID for example.

Further Exemplary Embodiments

One embodiment comprises a device, adapted with an internal property [RxSet] that determines if configuration has been applied to the device. Each time the device is powered on, the RxSet property is checked, if this is false the device will immediately communicate with the remote server to query for a configuration profile. During this process, which could take several minutes, an animation is shown on the display of the unit indicating that the device is configuring itself. During this process, any buttons or controls on the device are locked out, such that the patient must wait for the process to complete, and the device cannot provide therapy until the process completes. Once the downloaded configuration profile is confirmed with the server, a completion message is shown to the user before the device reverts to its normal standby mode. At this point the RxSet property is set to true, meaning that any subsequent time the device is powered up, it will immediately enter normal standby mode.

If the device is unable to communicate with the remote server, or unable to locate a configuration profile for its serial number, the device may retry the connection several times before displaying an error message such as "No prescription available, please contact your healthcare provider". In this case the RxSet property will retain its default false value, meaning any subsequent time the device is powered up, it will again attempt to connect and download a configuration profile.

It may be desirable that a patient is able to explore their device, learning about its functions while the prescription is being downloaded, rather than being locked out of the device completely until the device is configured. Another embodiment consists of a device as before, adapted with an internal property [RxSet] that determines if configuration has been applied to the device. Each time the device is powered on, the RxSet property is checked. If this is false the device will communicate with the remote server to query for a configuration profile. In this case however, the device will continue to start as normal entering standby mode while the communication with the remote server continues in the background. The device shows an Rx indicator symbol, with a line through it, on its display to indicate that device does not yet have settings configured. The patient can enter all device menus and explore the device as normal, however if they attempt to start therapy while the communication is still in progress, an animation is shown on the display of the unit indicating that the device is configuring itself and therapy will not be able to be started. The patient can still continue to explore other device features, just not start therapy. Once the configuration process is complete, the Rx symbol, with a line through it, disappears from the display and therapy can be started as normal. At this point the RxSet property is set to true, meaning that any subsequent time the device is powered up, it will enter normal standby mode and be able to provide therapy.

If the device is unable to communicate with the remote server, or unable to locate a configuration profile for its serial number, the device may retry the connection several times. If after retrying it is still unable to obtain a profile, an attempt to start therapy on the device will result in the device displaying an error message such as "No prescription available, please contact your healthcare provider" and therapy will not be able to be started however the patient can still continue to explore other device features, just not start therapy. The RxSet property will retain its default false value, meaning any subsequent time the device is powered up, it will again attempt to connect and download a configuration profile.

Another embodiment consists of a device that contains a default AUTO CPAP mode. AUTO CPAP mode is a mode where the device automatically titrates its pressure output to a therapeutic pressure based on occurrences of events. As before the device is adapted with an internal property [RxSet] that determines if configuration has been applied to the device. Each time the device is powered on, the RxSet property is checked, if this is false the device will communicate with the remote server to query for a configuration profile. During this process, which could take several minutes, the device is able to function normally and provide therapy in this default AUTO CPAP mode. The device will continue to operate in this mode until it successfully connects to the remote server and receives a configuration profile with updated therapeutic settings. At this point the RxSet property is set to true, meaning that any subsequent time the device is powered up it won't continue to connect and search a profile.

In all of these embodiments, at any time before a configuration profile is applied to a device, a provider is able to enter a secret "clinician mode" by entering a specific key combination on the device. Clinician mode enables a provider to manually set device prescription settings. Manually configuring a device sets the RxSet property in the device to true, allowing the device to enter normal standby mode and unlocking therapy delivery.

Another embodiment consists of a device that contains only a base firmware image, this base firmware image having functionality only to connect to the remote server and retrieve a configuration profile instructing it as to which full firmware image to download and install. When powered in this base firmware state, the device will communicate with the remote server to query for a configuration profile. During this process, which could take several minutes, an animation is shown on the display of the unit indicating that the device is configuring itself. The downloaded configuration profile instructs the device to download a full firmware image containing the operating firmware for the type of device that has been prescribed to the patient, for example an AUTO CPAP image or a Bi Level image. The device then downloads and installs this image, restarting into a therapeutically operable state. This embodiment allows for manufacture of one single model of device containing this base firmware. This device, when first powered, is then able to adapt itself to one of many possible models, providing the specific therapy mode and features required by the patient.

The ability for a device to connect and retrieve a configuration profile relies on the configuration profile for the patient and device being provisioned on the remote server. This is done through an online management system configured to communicate with a database.

In one embodiment, prior to a device being given or shipped to a patient, a healthcare provider is able to set a patient up in this management system through a website, tablet or mobile application. Adding a patient creates a patient object in the database consisting of:

```
Patient {
    firstName (string),
    lastName (string),
    dateOfBirth (string),
    initial (string, optional),
    reference (string, optional),
    gender (string, optional) = ['male', 'female', 'other'],
    height (number, optional),
    weight (number, optional),
    address (Address, optional)
}
Address {
    addressLine1 (string, optional),
    addressLine2 (string, optional),
    city (string, optional),
    state (string, optional),
    country (string, optional),
    fax (string, optional),
    zip (string, optional),
    homePhone (string, optional),
    workPhone (string, optional),
    mobilePhone (string, optional),
    otherPhone (string, optional),
    email (string, optional)
}
```

Each patient is given a unique ID, identifying them within the date structure.

Once a patient is created they can be assigned a device by serial number. A device could be assigned by entering its serial number through the interface of the application via a website, tablet or mobile application, or by using the camera on a tablet or mobile device to scan the barcode on the device or device packaging and extract the serial number of the device. Assigning a patient a device results in a device record being created in the database, and this being related to the patient by the patients Id. A device record consists of:

```
Device {
    serialNumber (string),
    therapyStartDate (string),
    patientId (number),
}
```

A configuration profile can then be created for a patient, by the provider, by selecting the patients prescribed settings or modes through this website, tablet or mobile interface. A configuration profile consists of a header, containing the serial number, model and family of the device it is provisioned for along with any or all of:

Device configuration settings (for example pressure set points, operating modes i.e., AUTO or CPAP, humidity set points).

Activation commands for therapeutic features (for example a code to enable a feature that is already present on a device but not active, such as SensAwake™, humidity)

Header data referencing paths of software modules the device should download to install additional features Header data referencing paths of firmware images the device should download to upgrade its operating software.

For example,

Device configuration settings:

```
<ConfigurationProfile>
    <Device>
        <SerialNumber>120101000001</SerialNumber>
        <Model>Auto</Model>
        <Family>ICON</Family>
        <CreationDateTime>12-01-01T12:00:00</CreationDateTime>
```

-continued

```
    </Device>
    <Settings>
        <OperatingMode>Cpap</OperatingMode>
        <SetPressure>12</SetPressure>
        <Humidity>5</Humidity>
    </Settings>
</ConfigurationProfile>
```

Feature activation commands:

```
<ConfigurationProfile>
    <Device>
        <SerialNumber>120101000001</SerialNumber>
        <Model>Auto</Model>
        <Family>ICON</Family>
        <CreationDateTime>12-01-01T12:00:00</CreationDateTime>
    </Device>
    <Features>
        <ActivateHumidity>true</ActivateHumidity>
    </Features>
</ConfigurationProfile>
```

Feature Modules:

```
<ConfigurationProfile>
    <Device>
        <SerialNumber>120101000001</SerialNumber>
        <Model>Auto</Model>
        <Family>ICON</Family>
        <CreationDateTime>12-01-01T12:00:00</CreationDateTime>
    </Device>
    <InstallModules>
        <Module>
            <Name>SensAwake</Name>
            <Path>/api/modules/icon/auto/sensawake</Path>
            <Checksum>8345FA8</Checksum>
        </Module>
    </InstallModules>
</ConfigurationProfile>
```

Firmware Updates:

```
</ConfigurationProfile>
    <Device>
        <SerialNumber>120101000001</SerialNumber>
        <Model>Auto</Model>
        <Family>ICON</Family>
        <CreationDateTime>12-01-01T12:00:00</CreationDateTime>
    </Device>
    <Firmware>
        >Version>1.3.2</Version>
        <Path>/api/modules/icon/auto/firmware/1_3_2</Path>
        <Checksum>8345FA8</Checksum>
    </Firmware>
</ConfigurationProfile>
```

Once a configuration profile is created, it is stored in the database indexed by device serial number. A configuration profile also has an associated status value, so that it can be tracked throughout its lifecycle. For example:

```
ConfigurationProfile {
    SerialNumber (string),
    ProfileData (xml),
    CreationDateTime (string),
    Status (string),
}
```

The status value allows the system to evaluate if a configuration profile has been applied to a device and confirmed as correct. Possible status values are:

PENDING—the Configuration Profile has been created but not requested by a device APPLIED—the configuration profile has been requested by a device CONFIRMED—the configuration profile has been confirmed as applied and accurate on a device.

In another embodiment, prior to a device being shipped to a patient, as before, a healthcare provider is able to set a patient up in this management system through a website, tablet or mobile application. Each patient is given a unique ID, identifying them within the date structure.

In this embodiment, rather than a device serial number being entered or scanned by the healthcare provider, an order for the device is created in the system. This order is able to be transmitted to a remote fulfilment centre. To create this order a healthcare provider is prompted to select a device model, enter a shipping address, and as before create a configuration profile for the patient. As this configuration profile does not yet have a serial number assigned, it is temporarily associated with the order. The patient's unique Id is added to the order allowing the order to be referenced back to the patient.

The order is transmitted to a fulfilment centre, running software adapted to communicate with the patient management server. On picking the order they scan or enter the provided order number and device serial number into this software, which communicates this information back to the remote server. On receiving this fulfilment information, the server retrieves the configuration profile associated with the order and updates it with the provided serial number.

When a device connects to the remote server, probably when first powered on at the patient's home, it provides a data structure containing its serial number back to the remote server. The server performs a lookup against the configuration profile database to see if a configuration profile exists for that serial number.

If a profile is found, the profile data is extracted from the database, encrypted, and returned to the device. The status value in the database for that configuration profile is set to APPLIED.

On receiving a profile, the device decrypts it and first checks the serial number, model and family contained in the header to ensure the profile is meant for this specific device. It then reads the creation date time, and compares it to the last date and time that a settings change was made on the device. If the prior settings change was of a more recent date than what is in the received profile, the profile is ignored. This prevents older profiles from being applied if the settings of the device were changed, for example, through the devices user interface, after the profile was created.

If the received profile contains a firmware element, the device will reconnect to the server using the path provided in the firmware element. This path references a firmware file that is incrementally downloaded to the device. Once the file is completely downloaded, a checksum of the downloaded file is calculated. If the checksum of the downloaded file matches the checksum provided in the configuration profile, the device installs the new firmware and restarts.

If the received profile contains an install module element, for each referenced module, the device will reconnect to the server using the path of the module provided in the module element. This path references a module file that is incrementally downloaded to the device. Once the module file is completely downloaded, a checksum of the downloaded file is calculated. If the checksum of the downloaded file matches the checksum provided in the configuration profile for that module, the device installs the new module, its functionality becoming available to the device.

If the received profile contains a feature activation element, each of the features referenced in the list are enabled, becoming available to the device.

If the received profile contains a settings element, each referenced setting is updated on the device.

Once the profile has been applied, the device connects again to the remote server returning the updated value of any settings that have been altered by the profile, and the versions of any modules or firmware that have been installed. The server compares these values to the values in the original profile that was returned to the device. If the values match, the status property in the database for that configuration profile is set to CONFIRMED.

The remote server is configured to check the status of a new configuration profile a predefined time period (for example 24 hours) after it was created. If when checked the status of the profile is not CONFIRMED, the healthcare provider is notified that a device has failed to retrieve its configuration within the allowed period. This notification may be through an alert being shown in the interface of the patient management system when the provider next logs on, or it may be by a text message, phone call, or e-mail automatically generated by the server.

The invention claimed is:

1. A system comprising:
a CPAP apparatus comprising a modem, device data comprising identification information of the pressure support device and a default configuration profile;
a remote server configured to communicate with a database; and
a computing device configured to receive patient data associated with a patient, patient device data corresponding to the device data, and patient configuration data comprising a patient configuration profile for the CPAP apparatus;
wherein the computing device is configured to provide the patient data, the patient device data and the patient configuration data to the database for storage, the patient data and patient configuration data being associated with the patient device data in the database,
wherein the CPAP apparatus is configured to communicate with the remote server via the modem upon first initialization of the CPAP apparatus to:
establish a connection with the remote server,
transmit the device data to the remote server, and
receive from the remote server, the patient configuration data,
wherein the CPAP apparatus is further configured to apply the configuration data such that the CPAP apparatus provides CPAP therapy according to a customized configuration profile, and
wherein the CPAP apparatus is configured to provide CPAP therapy according to the default configuration profile if the CPAP apparatus fails to communicate with the remote server to receive the patient configuration data.

2. The system of claim 1, wherein the remote server is configured to search the database for patient device data and retrieve the associated patient configuration data for transmission.

3. The system of claim 1, wherein the device data is stored on an internal memory of the CPAP apparatus.

4. The system of claim 1, wherein the device data comprises a device serial number.

5. The system of claim 1, wherein the patient device data comprises a device serial number.

6. The system of claim 1, wherein the modem is at least one of an internal modem and an external modem.

7. The system of claim 1, wherein the patient device data is, or is inferred from an identifying mark on the CPAP apparatus, or on packaging associated with the CPAP apparatus.

8. The system of claim 7, wherein the identifying mark is at least one of a two dimensional bar code and a QR code.

9. The system of claim 1, wherein the patient configuration data comprises at least one of:
a device configuration setting,
an activation command,
a software module, and
full or partial device firmware.

10. The system of claim 9, wherein the device configuration setting includes at least one of a therapy pressure set point, an operating mode, and a humidity set point.

11. The system of claim 9, wherein the CPAP apparatus comprises a disabled therapy feature, and the activation command comprises an instruction to enable the therapy feature.

12. The system of claim 9, wherein the software module comprises an application such that the CPAP apparatus can provide an additional therapy feature.

13. The system of claim 1, wherein the computing device comprises at least one of a personal computer, tablet, and mobile telephone.

14. A system comprising:
a pressure support device comprising a communications interface and device data comprising identification information of the pressure support device;
a remote server configured to communicate with a database; and
a user entry device configured to receive patient data associated with a patient, patient device data corresponding to the device data, and patient configuration data comprising a patient configuration profile for the pressure support device,
wherein the user entry device is configured to provide the patient data, the patient device data and the patient configuration data to the database for storage, the patient data and patient configuration data being associated with the patient device data in the database,
wherein the pressure support device is configured to communicate with the remote server via the communications interface upon first initialization of the pressure support device to:
establish a connection with the remote server,
transmit the device data to the remote server, and
receive from the remote server, the patient configuration data,
wherein the pressure support device is further configured to apply the configuration data such that the pressure support device provides pressure therapy according to a customized configuration profile.

15. The system of claim 14, wherein the pressure support device comprises a default configuration profile, and is configured to provide pressure therapy according to the default configuration profile if the pressure support device fails to communicate with the remote server to receive the patient configuration data.

16. The system of claim 14, wherein the remote server is configured to search the database for patient device data and retrieve the associated patient configuration data for transmission.

17. The system of claim 14, wherein the device data is stored on an internal memory of the pressure support device.

18. The system of claim 14, wherein the device data comprises a device serial number.

19. The system of claim 14, wherein the patient device data comprises a device serial number.

20. The system of claim 14, wherein the communications interface comprises at least one of an internal modem and an external modem.

21. The system of claim 14, wherein the patient device data is, or is inferred from an identifying mark on the pressure support device, or on packaging associated with the pressure support device.

22. The system of claim 21, wherein the identifying mark is at least one of a two dimensional bar code and a QR code.

23. The system of claim 14, wherein the patient configuration data comprises at least one of:
 a device configuration setting,
 an activation command,
 a software module, and
 full or partial device firmware.

24. The system of claim 23, wherein the device configuration setting includes a therapy pressure set point, an operating mode and a humidity set point.

25. The system of claim 23, wherein pressure support device comprises a disabled therapy feature, and the activation command comprises an instruction to enable the therapy feature.

26. The system of claim 23, wherein the software module comprises an application such that the pressure support device can provide an additional therapy feature.

27. The system of claim 14, wherein the user entry device comprises at least one of a personal computer and tablet.

* * * * *